(12) United States Patent
Regan

(10) Patent No.: US 8,298,763 B2
(45) Date of Patent: Oct. 30, 2012

(54) AUTOMATED HIGH-THROUGHPUT FLOW-THROUGH REAL-TIME DIAGNOSTIC SYSTEM

(75) Inventor: John Frederick Regan, San Mateo, CA (US)

(73) Assignee: Lawrence Livermore National Security, LLC, Livermore, CA (US)

(*) Notice: Subject to any disclaimer, the term of this patent is extended or adjusted under 35 U.S.C. 154(b) by 681 days.

(21) Appl. No.: 12/038,109

(22) Filed: Feb. 27, 2008

(65) Prior Publication Data

US 2008/0254467 A1    Oct. 16, 2008

Related U.S. Application Data

(60) Provisional application No. 60/904,505, filed on Mar. 2, 2007.

(51) Int. Cl.
*C12Q 1/68* (2006.01)
*B01L 3/00* (2006.01)
*B01L 99/00* (2010.01)
*B01D 21/00* (2006.01)

(52) U.S. Cl. ............... 435/6.1; 435/283.1; 422/68.1; 422/501; 422/527; 422/537; 422/539; 536/23.1

(58) Field of Classification Search ............. None
See application file for complete search history.

(56) References Cited

U.S. PATENT DOCUMENTS

| | | | |
|---|---|---|---|
| 5,234,809 A | | 8/1993 | Boom et al. |
| 5,589,136 A | * | 12/1996 | Northrup et al. ........... 422/102 |
| 5,695,720 A | * | 12/1997 | Wade et al. ............... 422/82 |
| 5,922,536 A | * | 7/1999 | Nivens et al. .............. 435/6 |
| 6,576,459 B2 | | 6/2003 | Miles et al. |
| 2003/0032172 A1 | | 2/2003 | Colston, Jr. et al. |
| 2004/0038385 A1 | * | 2/2004 | Langlois et al. ........... 435/287.1 |
| 2006/0057599 A1 | | 3/2006 | Dzenitis et al. |
| 2006/0148063 A1 | | 7/2006 | Fauzzi et al. |
| 2007/0068573 A1 | * | 3/2007 | Cox et al. ................ 137/1 |
| 2009/0137047 A1 | * | 5/2009 | Regan et al. ............. 436/48 |

FOREIGN PATENT DOCUMENTS

WO    WO 03/027325    * 4/2003

OTHER PUBLICATIONS

Miller, Judith, "U.S. Is Deploying a Monitor System for Germ Attacks", The New York Times, Jan. 22, 2003.
Cole, Sally, "Biodetectors Evolving, Monitoring U.S. Cities", Homeland Security Solutions, May 2003.

* cited by examiner

*Primary Examiner* — Betty Forman
(74) *Attorney, Agent, or Firm* — Eddie B. Scott

(57) ABSTRACT

An automated real-time flow-through system capable of processing multiple samples in an asynchronous, simultaneous, and parallel fashion for nucleic acid extraction and purification, followed by assay assembly, genetic amplification, multiplex detection, analysis, and decontamination. The system is able to hold and access an unlimited number of fluorescent reagents that may be used to screen samples for the presence of specific sequences. The apparatus works by associating extracted and purified sample with a series of reagent plugs that have been formed in a flow channel and delivered to a flow-through real-time amplification detector that has a multiplicity of optical windows, to which the sample-reagent plugs are placed in an operative position. The diagnostic apparatus includes sample multi-position valves, a master sample multi-position valve, a master reagent multi-position valve, reagent multi-position valves, and an optical amplification/detection system.

21 Claims, 14 Drawing Sheets

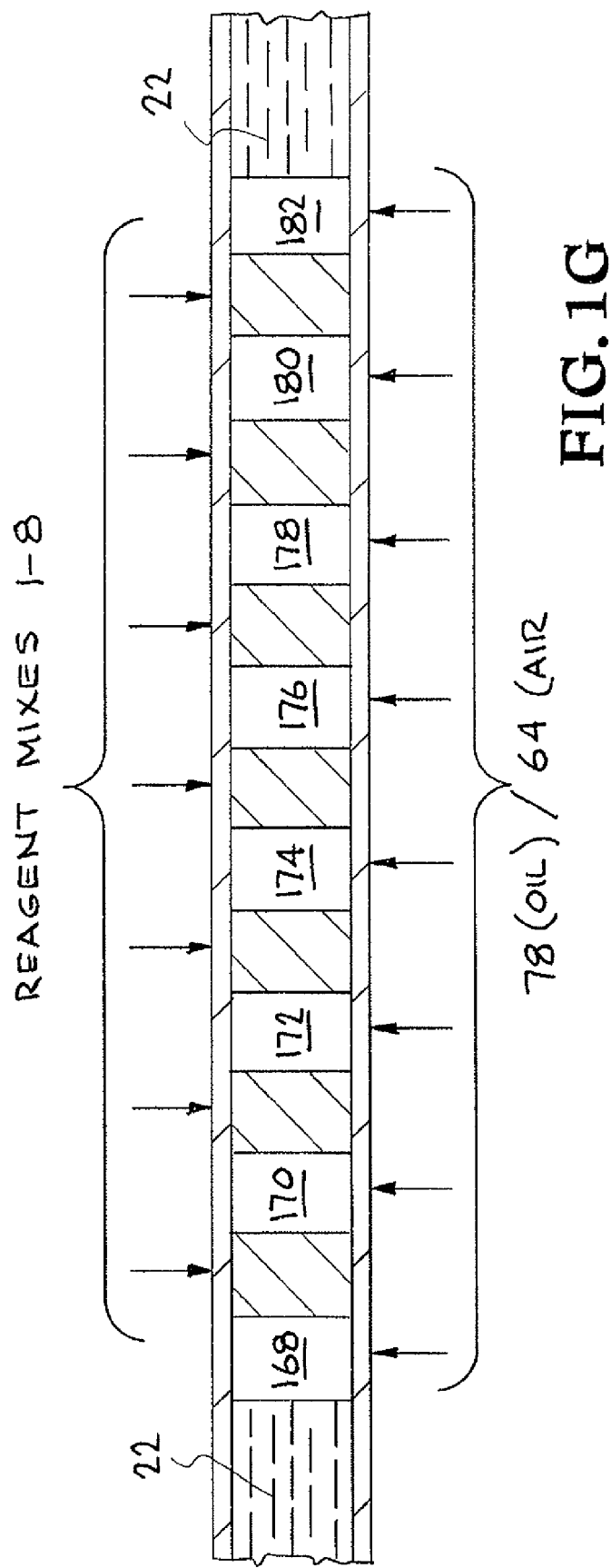

AUTOMATED HIGH-THROUGHPUT FLOW-THROUGH REAL-TIME DIAGNOSTIC SYSTEM

CROSS-REFERENCE TO RELATED APPLICATIONS

This application claims the benefit of U.S. Provisional Patent Application No. 60/904,505 filed Mar. 2, 2007 by John Frederick Regan titled "Automated High-Throughput Flow-Through Real-Time Fluorescence Detector." U.S. Provisional Patent Application No. 60/904,505 filed Mar. 2, 2007 by John Frederick Regan titled "Automated High-Throughput Flow-Through Real-Time Fluorescence Detector is incorporated herein by this reference.

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to diagnosis and more particularly to diagnostic instruments.

2. State of Technology

U.S. Pat. No. 5,234,809 issued to Willem R. Boom et al for a process for isolating nucleic acid provides the following state of technology information: "Known methods of isolating nucleic acid (NA) from complex starting materials like whole blood, blood serum, urine or feces usually comprise lysis of biological material by a detergent in the presence of protein degrading enzymes, followed by several extractions with organic solvents, e.g., phenol and/or chloroform, ethanol precipitation and dialysis of the nucleic acids. These known methods of, e.g., isolating (double-stranded) DNA from clinical material are very laborious and time-consuming. The relatively large number of steps required to purify NA from such starting materials increase the risk of transmission of NA from sample to sample in the simultaneous processing of several clinical samples. When the NA is isolated for the subsequent detection of the presence of NA of, e.g., a pathogen (e.g., a virus or a bacterium) by means of a nucleic acid amplification method for example the utmost sensitive polymerase-chain-reaction (PCR, Saiki et al, Science 230, 1985, 1350), the increased risk of such a transmission of NA between different samples which causes false positive results is a serious drawback."

United States Published Patent Application No. 2003/0032172 by Billy W. Colston, Jr. et al for an automated nucleic acid assay system provides the following state of technology information: "Nucleic acid amplification and detection is a widely used technique for conducting biological research. Utilization is applied to an increasing range of applications including diagnostics in bench-top research to the clinical arena, genomic screening for drug discovery to toxicology, screening for contamination to identification. Conventional sample preparation and analysis techniques for performing nucleic acid assays are time-consuming, require trained technicians, and lack precise repeatability. New technical developments are needed to improve the performance of nucleic acid amplification and detection . . . . Current instruments for performing chemical synthesis through thermal control and cycling are generally very large (table-top) and inefficient, and often they work by heating and cooling of a large thermal mass (e.g., an aluminum block). In recent years efforts have been directed to miniaturization of these instruments by designing and constructing reaction chambers out of silicon and silicon-based materials (e.g., silicon, nitride, polycrystalline silicon) that have integrated heaters and cooling via convection through the silicon . . . . A problem with standard PCR laboratory techniques is that the PCR reactions may be contaminated or inhibited by the introduction of a single contaminant molecule of extraneous DNA, such as those from previous experiments, or other contaminants, during transfers of reagents from one vessel to another. Also, PCR reaction volumes used in standard laboratory techniques are typically on the order of 50 microliters. A thermal cycle typically consists of four stages: heating a sample to a first temperature, maintaining the sample at the first temperature, cooling the sample to a second lower temperature, and maintaining the temperature at that lower temperature. Typically, each of these four stages of a thermal cycle requires about one minute, and thus to complete forty cycles, for example, is about three hours. Thus, due to the large volume typically used in standard laboratory procedures, the time involved, as well as the contamination possibilities during transfers of reagents from one vessel to another, there is clearly a need for microinstruments capable of carrying out the PCR procedure."

United States Published Patent Application No. 2006/0057599 by John Dzenitis et al for a system for autonomous monitoring of bioagents provides the following state of technology information: "There exists a critical need to develop distributed biothreat agent sensor networks that can operate in civilian applications. To operate in "Detect to Protect/Warn" type detection architectures, these platforms need to have several key properties. They need to be capable of detecting pathogens within a 1-2 hour time window, allowing for enough time to respond to an event. They need to be extremely low cost to maintain, since continuous monitoring is essential for many applications. These platforms need to have sufficient sensitivity to cover a broad geographical area (limiting the necessary number of sensors) and have sufficient selectivity to virtually eliminate false positives. Currently available bioweapons detection systems are designed primarily for military use on the battlefield. These systems are often expensive to deploy and ultimately unsuited for civilian protection.

In an article titled, "U.S. Is Deploying a Monitor System for Germ Attacks," by Judith Miller in The New York Times on Jan. 22, 2003, it was reported, "To help protect against the threat of bioterrorism, the Bush administration on Wednesday will start deploying a national system of environmental monitors that is intended to tell within 24 hours whether anthrax, smallpox and other deadly germs have been released into the air, senior administration officials said today . . . . The new environmental surveillance system uses monitoring technology and methods developed in part by the Department of Energy's national laboratories. Samples of DNA are analyzed using polymerase chain reaction techniques, which examine the genetic signatures of the organisms in a sample, and make rapid and accurate evaluations of that organism . . . . Officials who helped develop the system said that tests performed at Dugway Proving Ground in Utah and national laboratories showed that the system would almost certainly detect the deliberate release of several of the most dangerous pathogens."

United States Published Patent Application No. 2007/0148649 by Keiji Shigesada et al for a Cartridge for nucleic acid separation and purification and method for producing the same provides the following state of technology information: "Though nucleic acid has been used in various forms in various fields, it is often the case that only a trace amount of nucleic acid can be obtained, while operations of separation and purification are complicated and time-consuming."

In an article titled, "Biodetectors Evolving, Monitoring U.S. Cities," by Sally Cole in the May 2003 issue of homeland Security Solutions, it was reported, "The anthrax letter attacks of 2001, and subsequent deaths of five people, brought home the reality of bioterrorism to Americans and provided a wake-up call for the U.S. government about the need for a method to detect and mitigate the impact of any such future attacks. Long before the anthrax letter attacks, scientists at two of the U.S. Department of Energy's national laboratories, Lawrence Livermore National Laboratory (LLNL) and Los Alamos National Laboratory (LANL), were busy pioneering a "biodetector" akin to a smoke detector to rapidly detect the criminal use of biological agents."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a system for detecting different genetic assays in a sample. A flow channel is provided. A series of reagent plugs are formed in the flow channel. Sample preparation fluids are associated with the sample. The sample is associated with the reagent plugs forming sample-reagent plugs. In some embodiments the sample-reagent plugs are thermal-cycled to amplify the sample. Other embodiments achieve amplification under isothermal conditions and others do not require amplification. The pathogens in the sample/sample-reagent plugs are detected using optical detection. In some embodiments the optical detector has multiple optical windows and the sample-reagent plugs are positioned in operative position to the multiple optical windows for detecting different genetic sequences in the sample.

Some embodiments including the step of detecting sequences in additional samples by forming additional series of additional reagent plugs in additional flow channels, associating additional sample preparation fluids with the additional samples, associating the additional samples with the additional reagent plugs forming additional sample-reagent plugs, positioning the additional sample-reagent plugs in operative position to the multiplicity of optical windows in the detector for detecting different genetic sequences in the additional samples. In some embodiments the steps of positioning the sample-reagent plugs in operative position to the multiplicity of optical windows in the detector for detecting different genetic sequences in a sample, detecting the sequences in the sample in the sample-reagent plugs, positioning the additional sample-reagent plugs in operative position to the multiplicity of optical windows in the detector for detecting different genetic sequences in additional samples, and detecting the sequences in the samples in the additional sample-reagent plugs are performed asynchronously, simultaneously, and in parallel.

One embodiment of the system of the present invention is a diagnostic apparatus for detecting different genetic sequences in samples. The diagnostic apparatus includes an optical detector; sources of sample preparation fluids and reagent fluids; a master sample multi-position valve; sample multi-position valves for receiving and processing samples, the sample multi-position valves are connected to the optical detector, to the sources of sample preparation fluids and reagent fluids, and to the master sample multi-position valve; reagent multi-position valves are connected to the sources of sample preparation fluids and reagent fluids, a master reagent multi-position valve connected to the master sample multi-position valve and to the reagent multi-position valves; and heated and thermal-cycling elements connected to the sample multi-position valves and to the optical detector. In various embodiments, the multi-position valves are rotational directional valves.

The system is not based on a disposable plate format, and is capable of asynchronously running many different samples. The system creates little solid waste and most of the waste is liquid. The system can be programmed to decontaminate itself between individual runs. The system can run indefinitely as long as reagents are replenished and waste is removed and the number of runs that can be run between replenishing and disposing of waste is only dependant on the size of the reagent bottles, waste bottles, and the stability of the reagents, which can be extended with proper temperature storage conditions.

The system is modular and can be expanded to asynchronously process a high number of samples at a time, and an unlimited number of reagents to detect different genetic sequences may be stored within and utilized by the invention. The system is completely automated and links together nucleic acid extraction, concentration, and purification, with assay assembly, amplification, multiplex detection, analysis, and decontamination; all in a flow-through format.

The system can be used to detect any genetic sequence, including human or animal pathogens, differences among human genes (e.g. cancer causing mutations), and bio-warfare agents. The system permits asynchronous detection, meaning that if the invention is placed into an emergency room, one patient experiencing an influenza-like illness could have a sample taken by a healthcare provider and the sample could be placed on the instrument, and processing would begin immediately. If a second (third, and fourth, etc,) patient were to enter the same emergency room, either at the same time or spaced out by several minutes, the healthcare provider could take their samples and place them on the instrument and begin processing the samples almost immediately, without disrupting or delaying the diagnostic assay that had already begun on the sample from the first patient. The modular system has relatively few moving parts, and as a result, is reliable and not prone to breakage. If a modular part does break, replacing the modular part is relatively simple and could be performed in the "field" without special equipment.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIGS. 1A, 1B, 1C, 1D, 1E, 1F, and 1G illustrate an embodiment of the present invention.

DETAILED DESCRIPTION OF THE INVENTION

Figure 1A:
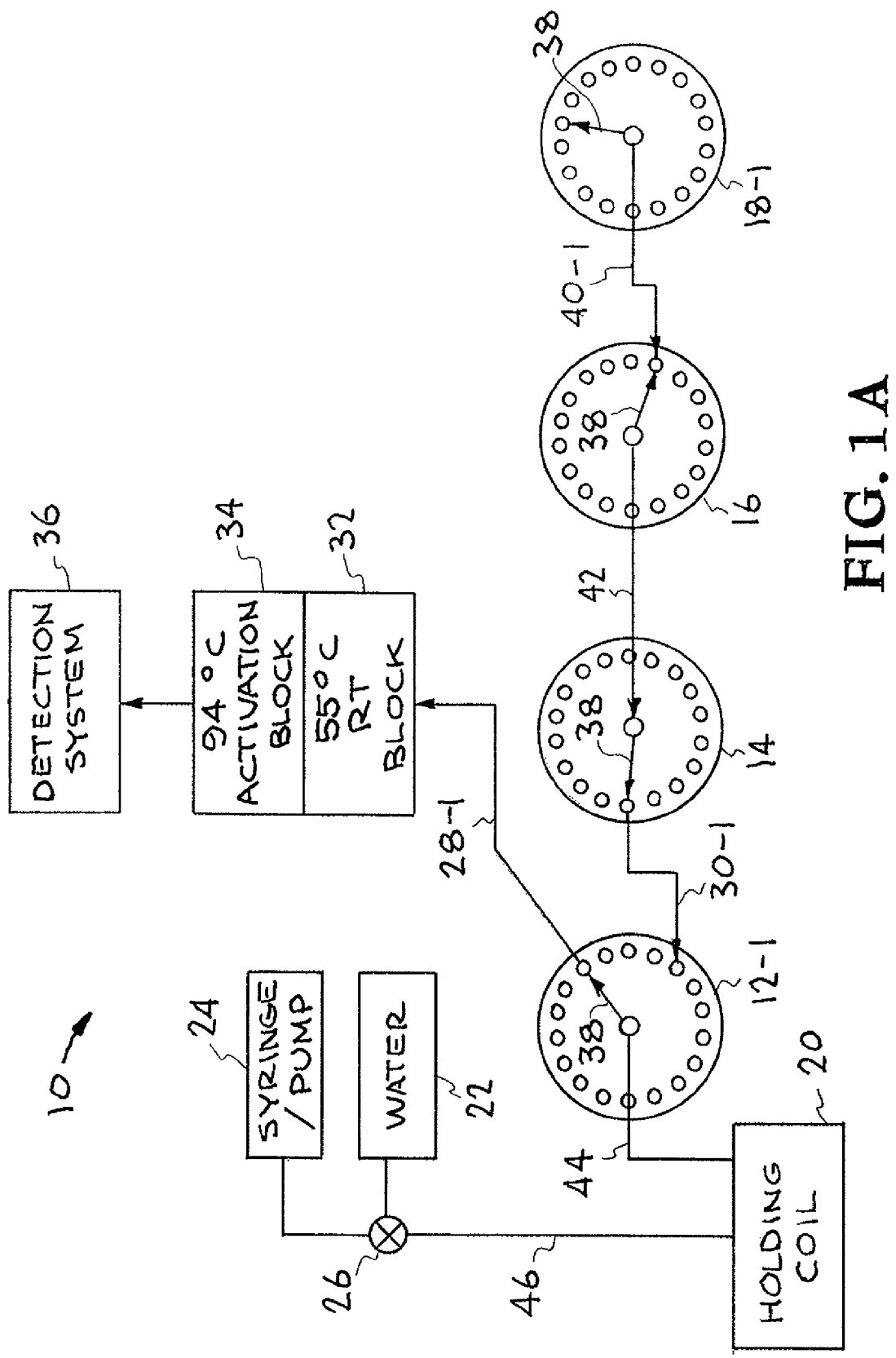

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Physical Description of the Diagnostic System—Referring now to the drawings and in particular to FIG. 1, one embodiment of a Diagnostic System that is able to detect the presence of a wide range of different sequences constructed in accordance with the present invention is illustrated. The Diagnostic System is designated generally by the reference numeral 10. The Diagnostic System (10) is a diagnostic apparatus for detecting different genetic sequences in a sample. The diagnostic apparatus includes an optical detector; sources of sample preparation fluids and reagent fluids; a master sample multi-position valve; a sample multi-position valve for receiving and processing the sample, the sample multi-position valve connected to the optical detector, to the sources of sample preparation fluids and reagent fluids, and to the master sample multi-position valve; a reagent multi-position valve connected to the sources of sample preparation fluids and reagent fluids, a master reagent multi-position valve connected to the master sample multi-position valve and to the reagent multi-position valve; and heated and thermal-cycling elements connected to the sample multi-position valve and to the optical detector. In various embodiments, the multi-position valves are rotational directional valves.

The Diagnostic System (10) is an automated, computer-controlled instrument designed to detect the presence of genetic sequences within samples. The system is largely composed of multi-position valves, syringe pumps, and lines. The number of these components corresponds to the number of samples the system can process and screen, as well as the number of accessible genetic reagents to perform the screening. In addition to these components, the Diagnostic System also requires heated and thermal-cycling elements and an optical detector system. The system is able to utilize single-use multi-barrel nucleic acid extraction cartridges, which are not required for operation, but do greatly improve the performance of the system.

The embodiment of the invention described here is a 12 channel instrument, although other embodiments with more than 12 channels can easily be envisioned. The term 'channel' is defined as all of the lines through which one syringe pump can move fluid, including the lines accessible by turning the valves' rotors to different positions. Each channel of the instrument is able to access lines unique to its channel, as well as lines shared amongst all the channels. A single 'channel' can be comprised of more than 37 lines. These lines are illustrated in FIG. 1A-G, and FIG. 2-5, where syringe pump (24) can move fluid through lines (28-1), (30-1), (40-1), (42), (44), (46), (73), (75), (84), (86), (88), (90), (92), (94), (96), (98), (100), (106), (108), (110), (112), (118), (119), (142), (144), (145), (146), (148), (150), (152), (154), (156), (158), (160), (162), (164), and (166).

Each channel is responsible for moving all the necessary fluids required to process and screen a particular sample for the presence of genetic sequences. Only one sample may be processed per channel at a time, but multiple channels may be simultaneously operational. The processing of each sample occurs independently of the other samples on the instrument, but each channel must sequentially access some components of the instrument that are shared amongst channels, including the reagents stored off valve (18-1), and the activities of valves (14), (16), and (216).

Microfluidics Background—Syringe pumps are used to draw, push, send, deliver, and expel fluids and air throughout the system. The use of these terms implies the active movement of a syringe pump and indicates the valves' rotors are in the necessary position to achieve the desired result. In general, the lines of the Diagnostic System (10) are filled with a carrier fluid (e.g. water (22)), regardless of whether they are currently in use. Large quantities of carrier fluid are used to help manipulate very small quantities of reagents. The term 'line' is used synonymously with tubing or microchannels that may be etched or in some way imprinted on a chip.

The manipulation of fluids throughout the Diagnostic System relies on the ability to keep different liquids within the same line separate. To achieve adequate separation, either oil (78) (e.g. mineral oil) or air (64) can be used to create a barrier on either side of the liquid of interest to prevent mixing of neighboring fluids within the system. Oil is often preferred since it does not compress or expand with changes in temperature or pressure. However, air must be used in the multi-barrel nucleic acid extraction cartridge (62), to prevent changes to the binding properties of the cartridge's filters (136 & 138) and silica pack (140). Air can be used throughout the entire system, but care must be taken to account for changes in volume that occur with changes in temperature and pressure. In addition, air can become humidified during heating, which changes the concentration of the heated reagents neighboring the air pocket, potentially altering the desired chemistry.

The Diagnostic System (10) includes the components illustrated in FIGS. 1A-G and FIGS. 2-5.

Description of Figures—FIG. 1A: The core operational unit of the Diagnostic System (10) includes the following components:

12-1 Sample Valve 1 (FIG. 1B)
14- Master Sample Valve (FIG. 1C)
16- Master Reagent Valve (FIG. 1D)
18-1 Reagent Valve 1 (FIG. 1E)
20 Holding Coil 1
22- Water 24 Syringe Pump
26 Valve
28-1 Line
30-1 Line
32- ~55° C. Reverse Transcription Block (RT Block)
34- ~94° C. Activation Block (Activ. Block)
36- Detection System
38- Valve Position Arrow
40-1 Line
42- Line
44- Line
46- Line FIG. 1B: The 'sample valve 1' (12-1) of the Diagnostic System (10) includes the following components:
12-1 Sample Valve 1
20- Holding Coil 1
22- Water
24- Syringe Pump
26- Valve
28-1 Line (To FIG. 1A/RT Block (32), Activ. Block (34), System Detector (36))
30-1 Line (From FIG. 1A 14)
38- Valve Position Arrow
44- Line
46- Line
48-1 Sample 1
50- Enzymes
52- 2× Reaction Buffer
54- Ethanol
56- Master Mixing Chamber 3
58- Mixing Lysis Chamber 1
60- Elution Mixing Chamber 2
62- Multi-Barrel Cartridge
64- Air
66- Buffer 1
68- Bleach
70- Lysis Buffer 1
71- Lysis Buffer 2
72- Buffer 2
73- Line
74- Junction
75- Line (To FIG. 2./Master Waste 1 (210))
78- Oil
80- Sonication 1
82- Sonication 2
84- Line
86- Line
88- Line
90- Line
92- Line
94-1 Line
96- Line
98- Line
100- Line
106- Line
108- Line
110- Line (To FIG. 2./Master Waste 2 (212))
112- Line
118- Line
119- Line FIG. 1C: The 'Master Sample valve' (14) of the Diagnostic System (10) includes the following components:
14- Master Sample Valve
12-1 Sample Valve #1
12-2 Sample Valve #2
12-3 Sample Valve #3
12-4 Sample Valve #4
12-5 Sample Valve #5
28-1 Line (To FIG. 1A/Detector System (36))
28-2 Line (To FIG. 1A/Detector System (36))
28-3 Line (To FIG. 1A/D Detector System (36))
28-4 Line (To FIG. 1A/Detector System (36))
28-5 Line (To FIG. 1A/Detector System (36))
30-1 Line
30-2 Line
30-3 Line
30-4 Line
30-5 Line
32- ~55° C. Reverse Transcription Block (RT Block)
34- ~94° C. Activation Block (Activ. Block)
38- Valve Position Arrow
42- Line (From FIG. 1D/Master Reagent Valve (16))
48-1 Sample 1
48-2 Sample 2
48-3 Sample 3
48-4 Sample 4
48-5 Sample 5
94-1 Line
94-2 Line
94-3 Line
94-4 Line
94-5 Line FIG. 1D: The 'Master Reagent valve' (16) of the Diagnostic System (10) includes the following components:
16- Master Reagent Valve
18-1 Reagent Valve 1 (e.g. Respiratory Pathogen Panel)
18-2 Reagent Valve 2 (e.g. Bio-Threat Pathogen Panel)
18-3 Reagent Valve 3 (e.g. Bacterial Sepsis Pathogen Panel)
18-4 Reagent Valve 4 (e.g. Blood-borne Pathogen Pathogen Panel)
18-5 Reagent Valve 5 (e.g. Gastrointestinal Pathogen Pathogen Panel)
18-17 Reagent Valve 17 (e.g. Sexually Transmitted Diseases Pathogen Panel)
40-1 Line (To FIG. 1E/Reagent Valve (18))
40-2 Line
40-3 Line
40-4 Line
40-5 Line
40-17 Line
42- Line (To FIG. 1C/Master Sample Valve (14))

Figure 1B:
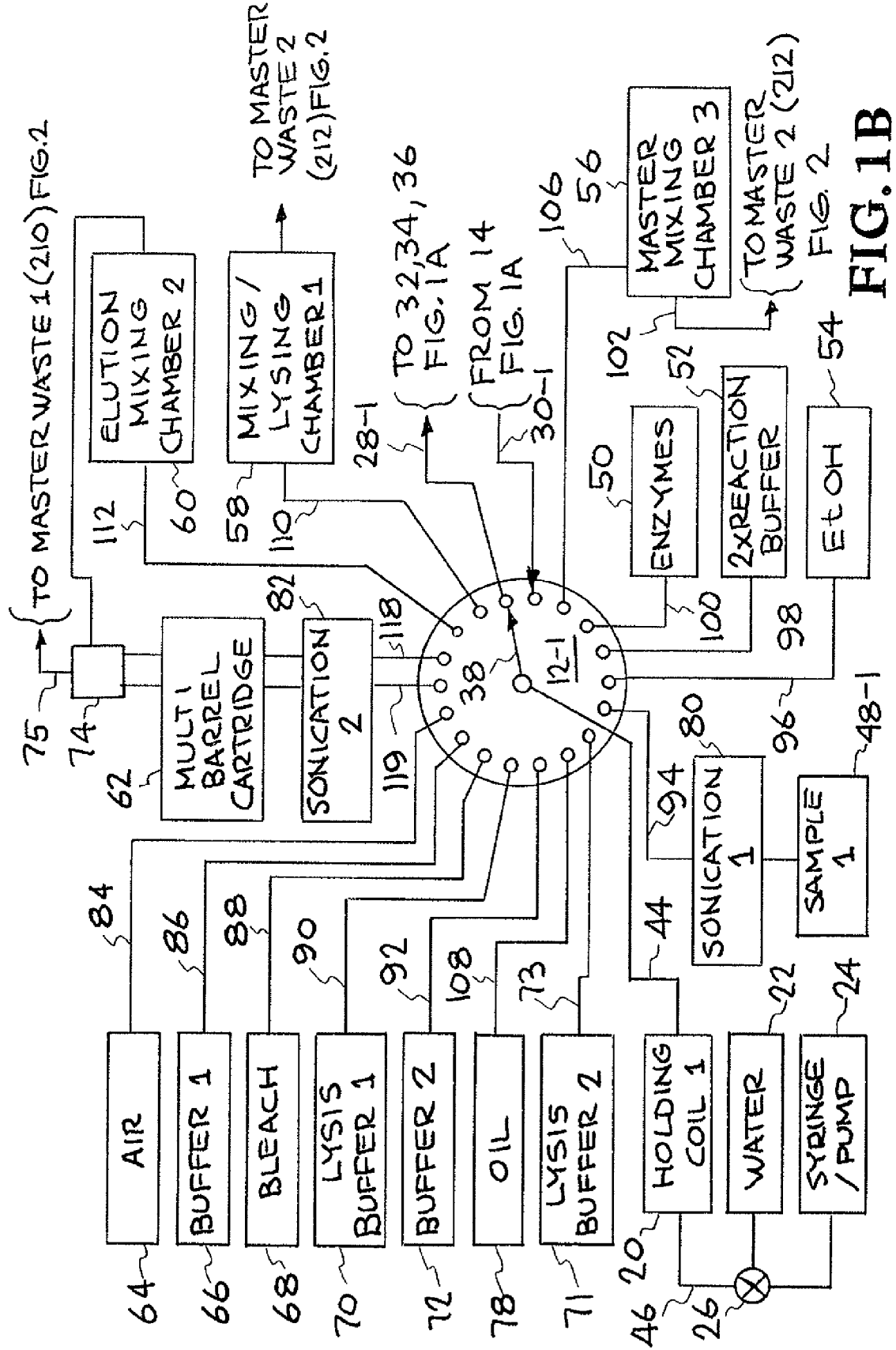
Figure 1C:
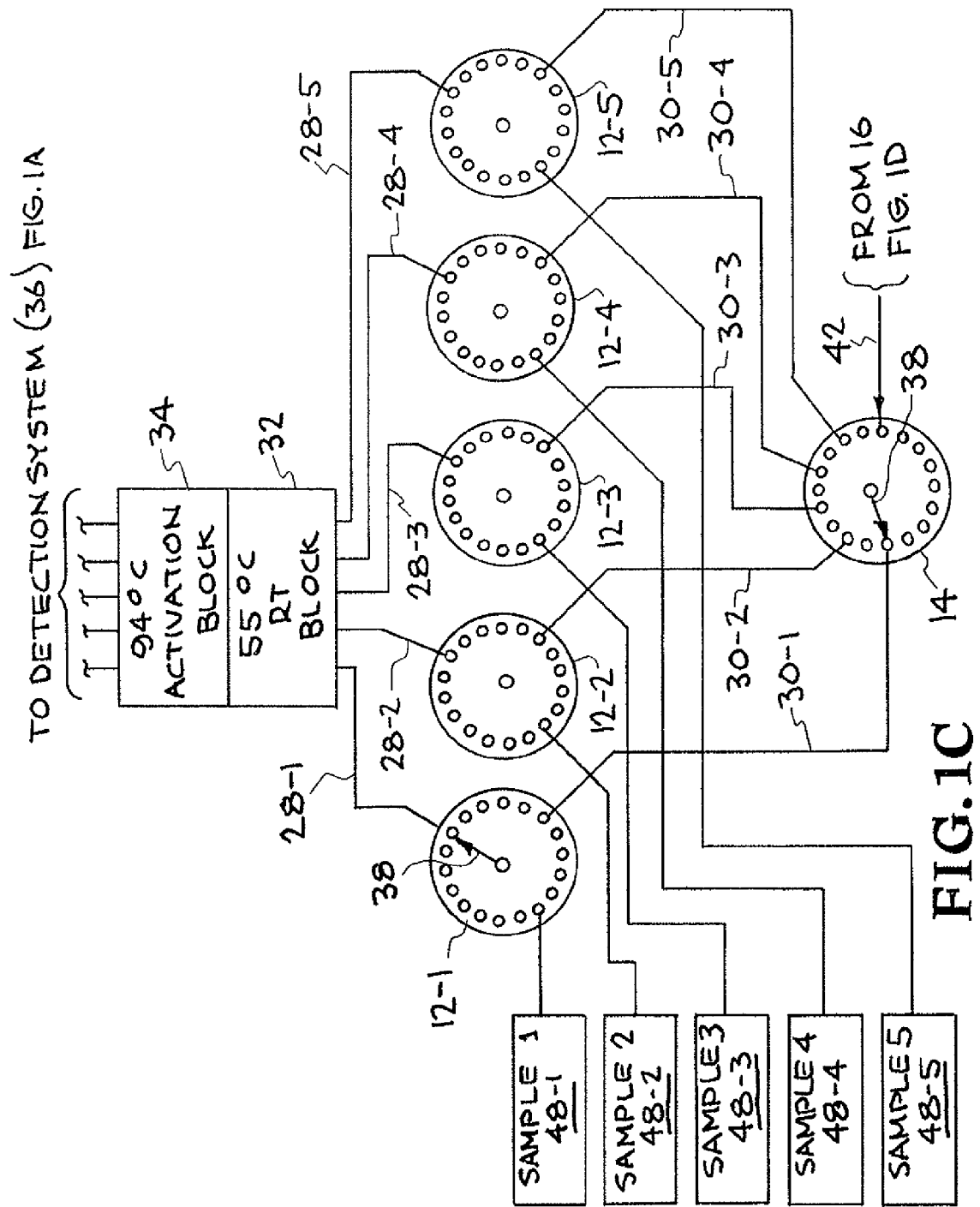
Figure 1D:
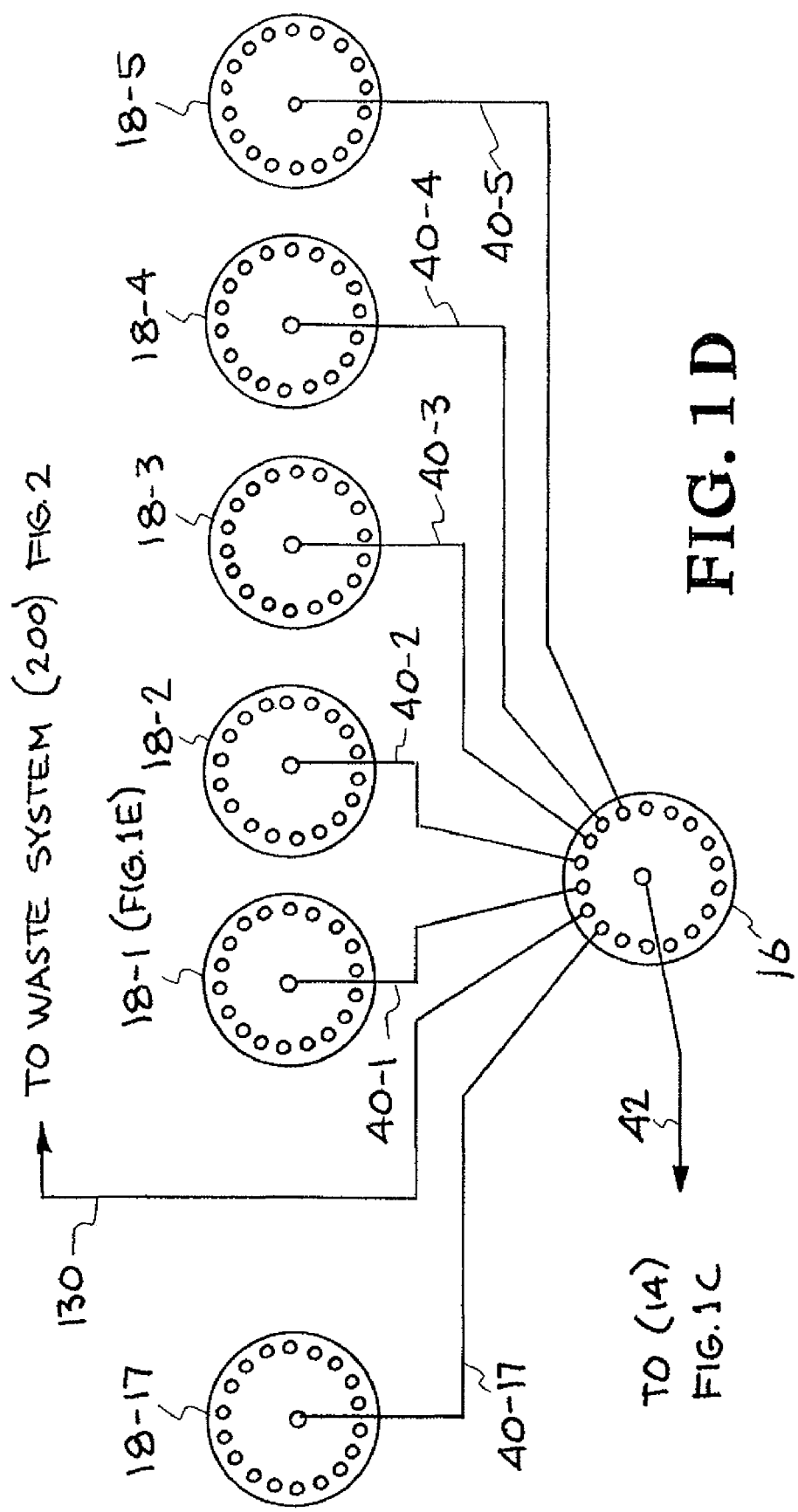
Figure 1E:
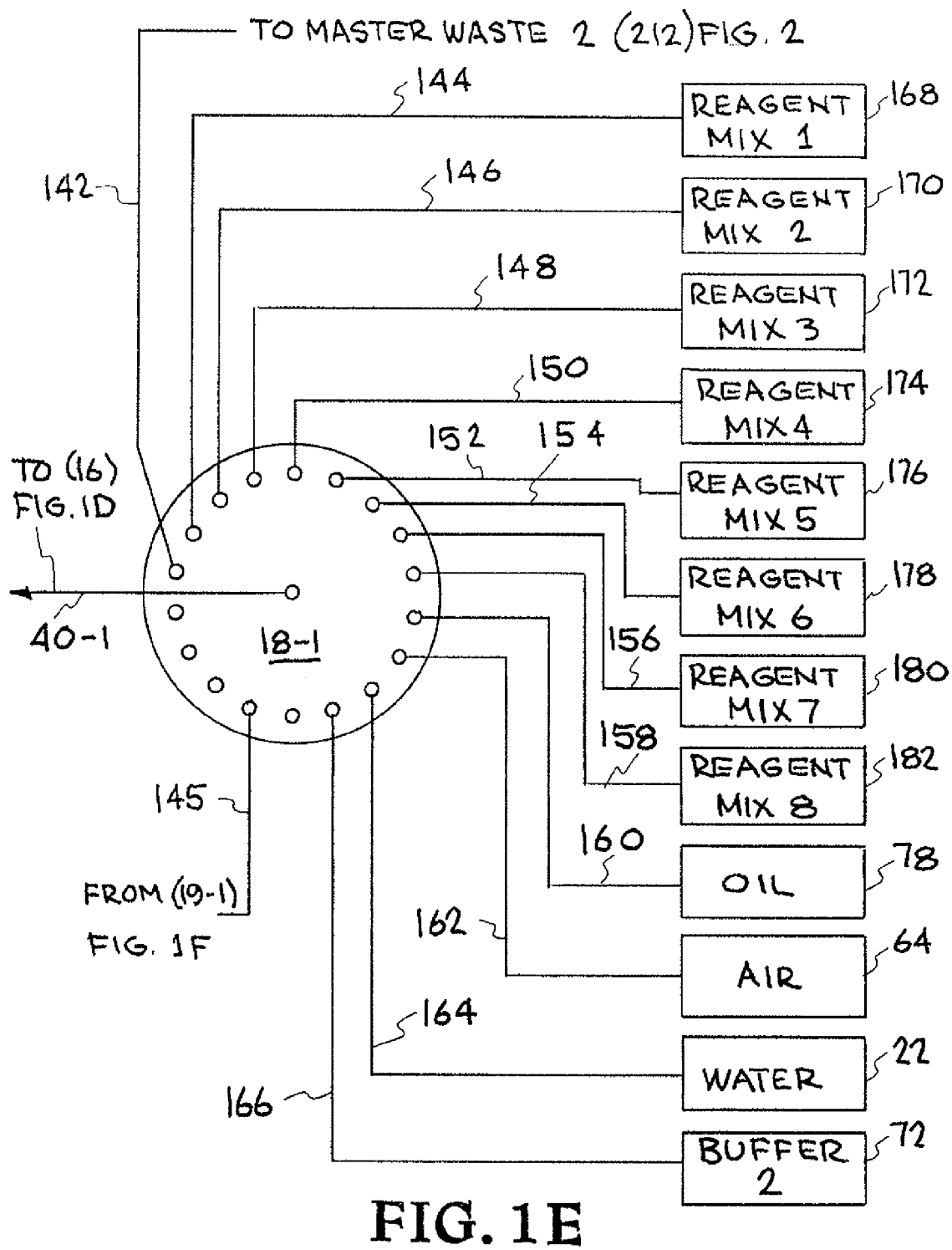

FIG. 1E: A 'reagent valve' (18-1, 18-2, etc.) of the Diagnostic System (10) holds the analyte-specific reagents in panel format. An example of a 'panel' is shown below, which includes 8 reagent mixtures. Each reagent mixture includes analyte-specific reagents for three different genetic signatures. The example shown is of a Respiratory Pathogen Panel, and includes influenza H1 subtype (H1), coronavirus (CoV), respiratory syncytial virus (RSV), adenovirus group B (Adeno B), all influenza A subtypes (Pan Flu A), influenza B (Flu B), influenza H5 subtype (H5), parainfluenza virus 1 (Para 1), parainfluenza virus 3 (Para 3), adenovirus group C (Adeno C), influenza H3 subtype (H3), metapneumovirus (MPV), rhinovirus (RhV), and adenovirus group E (Adeno E). Internal controls include: PCR Inhibition (PCR-1), Patient Sample Addition (PSA), Buffer Only Positive, and Buffer Only Negative. The size of the panel (number of mixtures) can be increased without limit, and the 'plex' of each mixture can be increased up to five analytes. Reagent valve 1 (18-1) includes the following components:
18-1 Reagent Valve 1
40-1 Line (To FIG. ID/Master Reagent Valve (16))

Figure 1F:
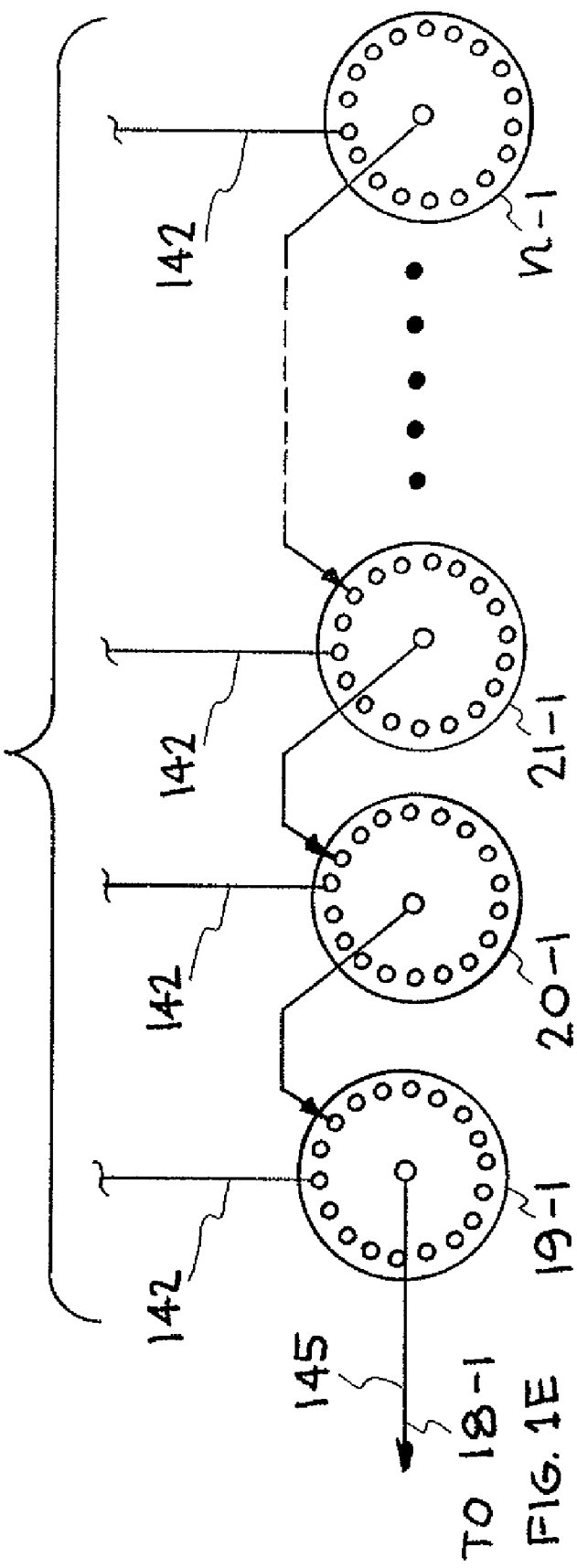
Figure 2:
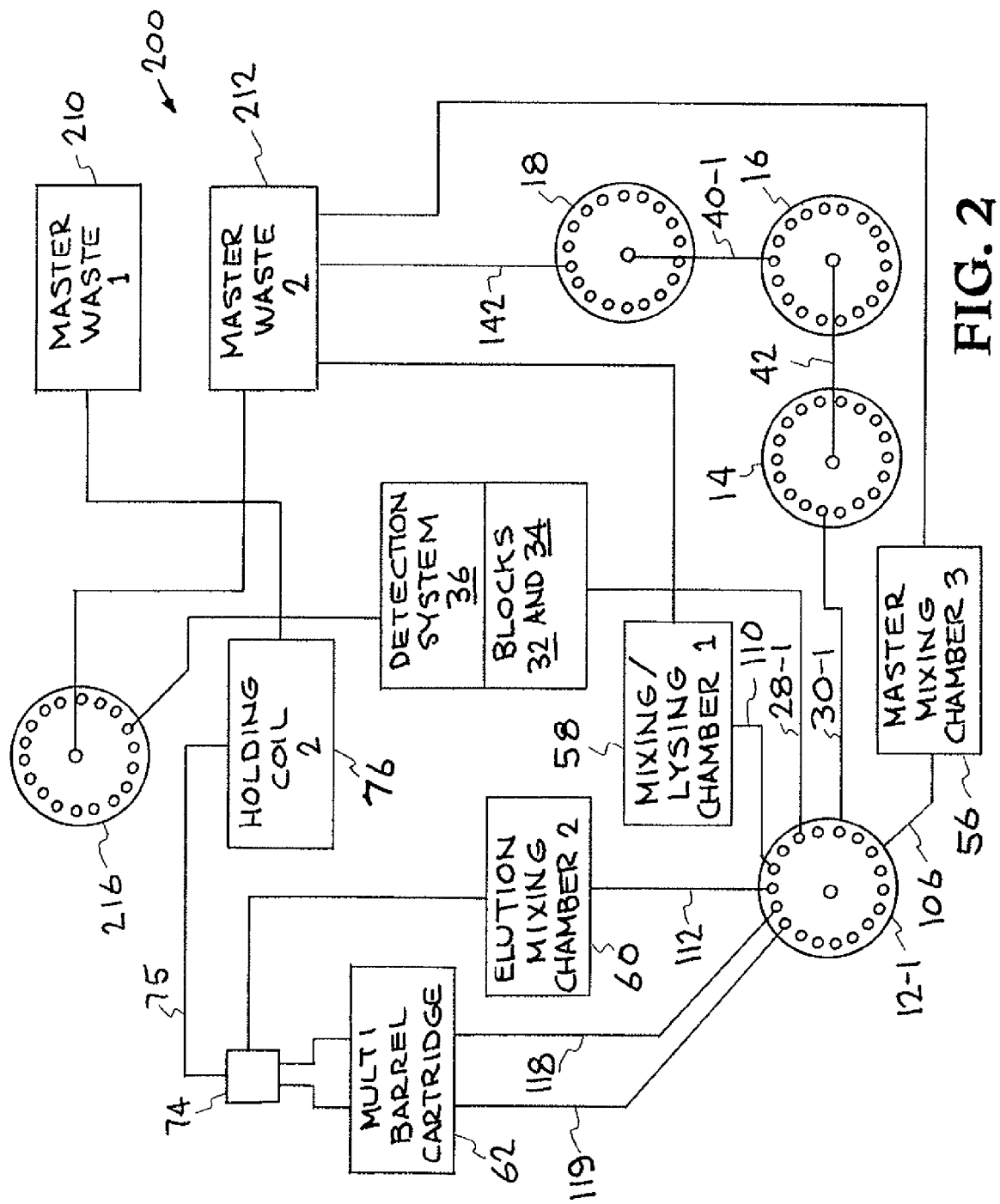
FIG. 2 illustrates the waste system of the present invention.
Figure 3:
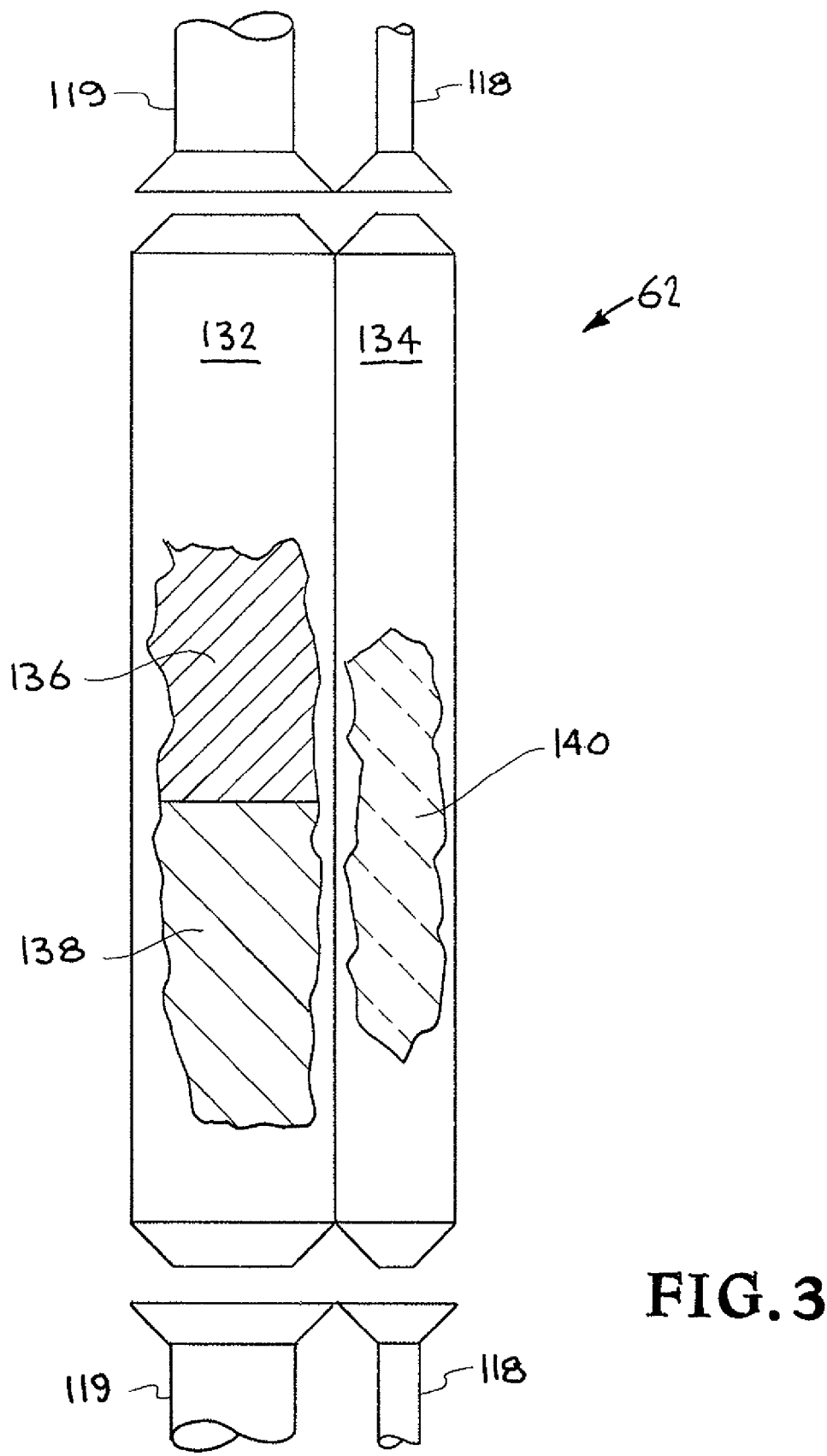
FIG. 3 illustrates a single-use multi-barrel nucleic acid extraction cartridge that may be incorporated into the present invention.

168- Reagent Mix #1 (e.g. Buffer only positive and negative control)
170- Reagent Mix #2 (e.g. 141, CoV, PCR-I)
172- Reagent Mix #3 (e.g. PSA, RSV, Adeno B)
174- Reagent Mix #4 (e.g. PSA, Pan Flu A, Flu B)
176- Reagent Mix #5 (e.g. H5, Para 1, PCR-I)
178- Reagent Mix #6 (e.g. PSA, Para 3, Adeno C)
180- Reagent Mix #7 (e.g. H3, MPV, PCR-I)
182- Reagent Mix #8 (e.g. PSA, RhV, Adeno EF)
78- Oil
64- Air
22- Water
72- Buffer 2
142- Line (To FIG. 2/Master Waste 2 (212))
144- Line
145- Line (From FIG. 1F/Daisy-Chained Reagent Valve (19-1))
146- Line
148- Line
150- Line
152- Line
154- Line
156- Line
158- Line
160- Line
162- Line
164- Line
166- Line FIG. 1F: Daisy-Chained Reagent Valves (19, 20, 21 . . . n) of the Diagnostic System (10) include the following components:

19-1 Daisy-Chained Reagent Valve 1-Layer 19
20-1 Daisy-Chained Reagent Valve 1-Layer 20
21-1 Daisy-Chained Reagent Valve 1-Layer 21
n-1 Daisy-Chained Reagent Valve 1-Layer n-1
142- Line (To FIG. 2/Master Waste 2 (212))
145- Line (To FIG. 1E/Reagent Valve 1 (18- 1)

Figure 4:
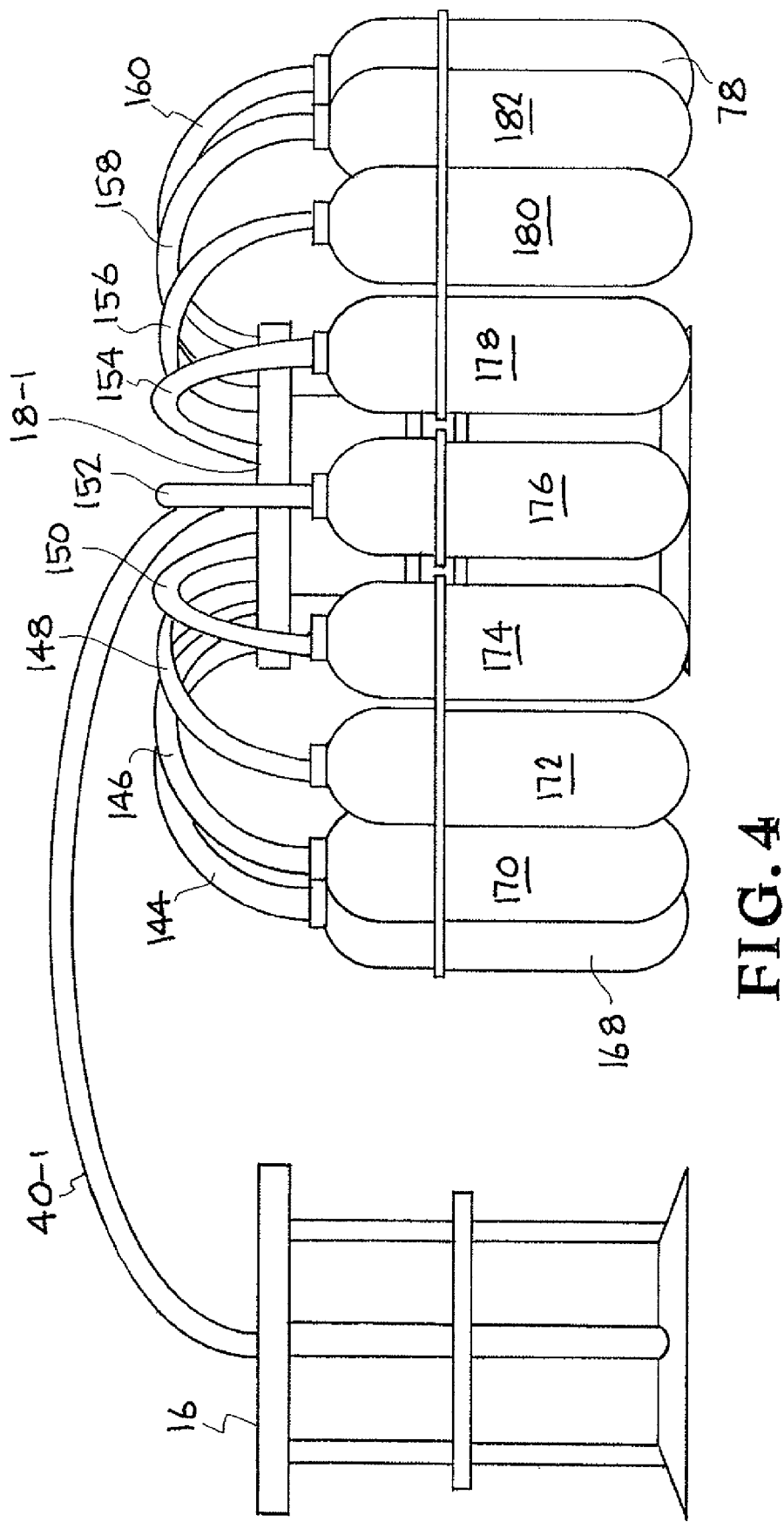
FIG. 4 illustrates a multi-position reagent valve of the present invention.
Figure 5:
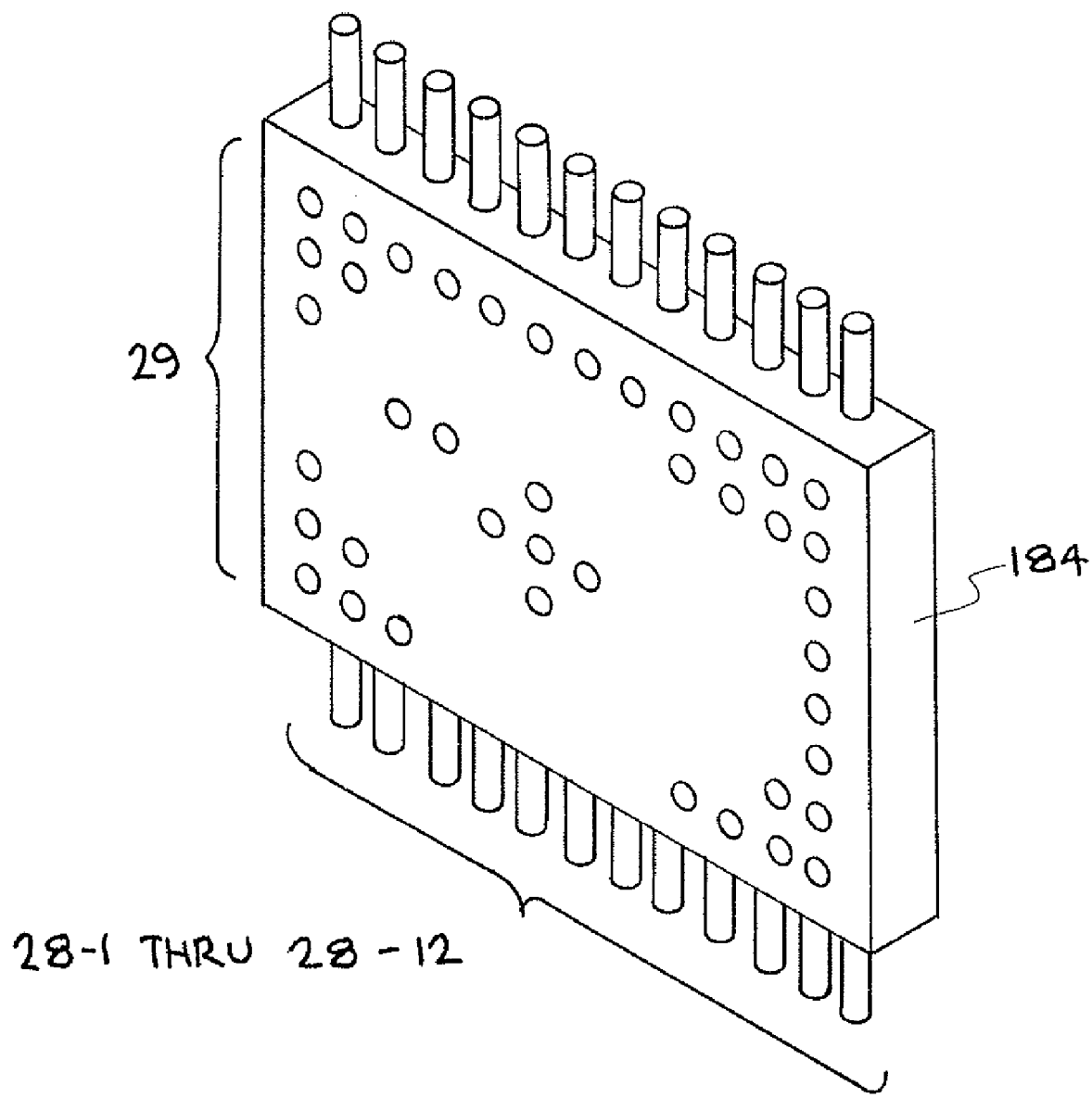
FIG. 5 illustrates the optical heating/cooling wafer that is a component of the optical detection system within the present invention.

FIG. 1G: A train of multiplex reagent mixtures that is moved through the lines of the Diagnostic System (10) includes eight different reagent mixtures separated by oil (or air). Carrier fluid (e.g. water) precedes and succeeds the train. The train is first formed in line 40-1, then moves through the Master Reagent valve (16), line (42), the Master Sample valve (14), through line (30-1), and into sample valve 1 (12-1), where Sample Master mix is added to each of the eight 3-plex reaction mixtures. The train is pulled into line (44) and holding coil 1 (20) during the addition of Sample Master Mix. The syringe pump (24) is then reversed and the train is delivered back through sample valve 1 (12-1) and directed into line (28-1), through the RT Block (32), the Activation Block (34), and into the Detection System (36) for amplification and optical monitoring. After the assay is complete, the train is delivered through waste valve (216) and into Master Waste 2 (212). A train of multiplex reagent mixtures is illustrated in FIG. 1G and includes the following components:

168- Reagent Mix #1 (e.g. Buffer only positive and negative control)
170- Reagent Mix #2 (e.g. H1, CoV, PCR-I)
172- Reagent Mix #3 (e.g. PSA, RSV, Adeno B)
174- Reagent Mix #4 (e.g. PSA, Pan Flu A, Flu B)
176- Reagent Mix #5 (e.g. H5, Para 1, PCR-I)
178- Reagent Mix #6 (e.g. PSA, Para 3, Adeno C)
180- Reagent Mix #7 (e.g. H3, MPV, PCR-I)
182- Reagent Mix #8 (e.g. PSA, RhV, Adeno E)
78- Oil
64- Air
22- Water FIG. 2: The 'Waste System' (200) of the Diagnostic System (10) includes the following components:
12-1 Sample Valve 1
14- Master Sample Valve
16- Master Reagent Valve
18-1 Reagent Valve 1
28-1 Line
30- Line
32- ~55° C. Reverse Transcription Block (RT Block)
34- ~94° C. Activation Block (Activ. Block)
36- Detection System
40-1 Line
56- Master Mixing Chamber 3
58- Mixing Lysing Chamber 1
60- Elution Mixing Chamber 2
62- Multi-Barrel Cartridge
74- Junction
76- Holding Coil 2
106- Line
112- Line
118- Line
119- Line
142- Line
210- Master Waste 1
212- Master Waste 2
216- Waste Valve FIG. 3: The Multi-Barrel Nucleic Acid Extraction Cartridge (62) of the Diagnostic System (10) includes the following components:
118- Line
119- Line
132- Left Barrel
134- Right Barrel
136- Fine Filter
138- Course Filter
140- Silica Pack FIG. 4: Multi-position valves (e.g. 12-1, 14, 16, 18-1, and 216) direct fluid flow throughout the Diagnostic System (10) by rotating a channeled rotor, which connects the central port to one of the peripheral ports. The central port is always 'active', whereas only one peripheral port is active at a time. The illustrated multi-position valve shows the peripheral ports hooked up to reagent mixtures; and fluid flow is possible in either direction. The vessels holding the reagent mixtures have vents to prevent vacuums from occurring when fluids are removed. The Diagnostic System can also utilize other valves that permit more complex fluid flow patterns, but for simplicity, single channel valves are shown. For descriptive purposes, an artist's rendition of the reagent valve (18-1) is shown in FIG. 4 and includes the following components:

16- Master Reagent Valve
18- Reagent Valve 1
40-1 Line (To FIG. 1D/Master Reagent Valve (16))
168- Reagent Mix #1 (e.g. Buffer only positive and negative control)
170- Reagent Mix #2 (e.g. H1, CoV, PCR-I)
172- Reagent Mix #3 (e.g. PSA, RSV, Adeno B)
174- Reagent Mix #4 (e.g. PSA, Pan Flu A, Flu B)
176- Reagent Mix #5 (e.g. H5, Para 1, PCR-I)
178- Reagent Mix #6 (e.g. PSA, Para 3, Adeno C)
180- Reagent Mix #7 (e.g. H3, MPV, PCR-I)
182- Reagent Mix #8 (e.g. PSA, RhV, Adeno E)
78- Oil
144- Line
146- Line
148- Line
150- Line 152- Line
154- Line
156- Line
158- Line
160- Line FIG. 5: The Detection System (36) of the Diagnostic System (10) can take many different forms. In this example, it is a flow-through thermal-cycler with a fluorescent optical monitoring unit, nearly identical to a conventional real-time thermal cycler. Examples of real-time thermal cyclers that could be modified for use as a Detection System (36) include: Bio-Rad Corporation's iQ5 Real-Time PCR Detection System and Applied Biosystems' 7900HT Fast Real-Time PCR System. Both perform 5-channel real-time detection. The former utilizes a 96-well format and the later utilizes a 384-well format. The 96-well format consists of 12 columns and 8 rows, and the 384-well format consists of 24 columns and 16 rows, The Detection System (36) could also utilize specially built thermal-cyclers that offer more columns and rows to expand the diagnostic capabilities of the system. The utilization of 96-well and 384-well real-time thermal-cyclers for the Detection System (10) allows different numbers of samples to be analyzed for different numbers of analytes. For a 96-well detector, either 12 samples could each be split into 8 reactions; or, 8 samples could each be split into 12 reactions, Likewise, for a 384-well detector, either 16 samples could each be split into 24 reactions; or, 24 samples could each be split into 16 reactions. A single reaction can screen for up to five different genetic sequences using quantitative real-time assays.

In order to make a commercially available thermal cycler usable as the Detection System (36) of the Diagnostic System (10), it must be modified to accept an optical heating/cooling wafer (184) rather than a conventional heating/cooling block that accepts disposable welled plates. The optical heating/cooling wafer has permanent optically transparent lines (e.g. tubing) that flow through the wafer in a horizontal fashion, in the same orientation as either the columns or rows of a conventional heating/cooling block. The tubing within the optical heating/cooling wafer carries trains of real-time reactions (or other assays). These reactions are spaced appropriately within the tubing and are moved to the appropriate location to allow for the optical monitoring. Optical monitoring occurs through holes (29) in the optical heating/cooling wafer that are in the same locations as the wells of a conventional heating/cooling block. The transparent tubing allows light to be directed into the tubing, and likewise, light may be transmitted back out of the tubing for detection. The optical heating/cooling wafer must have thermal properties similar to a conventional heating/cooling block and be capable of PCR amplification.

The Diagnostic System (10) could also utilize a Detection System (36) that remains at one temperature for isothermal amplification. Alternatively, the Diagnostic System could utilize Lab-on-a-Chip (LoaC) technology. In this form, amplification would be achieved by pushing and pulling the reaction mixtures back and forth through different heating zones to achieve amplification. This form eliminates the need to change the temperature of the thermal cycler and instead relies on moving the sample through different temperature zones to achieve amplification. In order for LoaC technology to effectively work in a 96-well format, different temperature zones would need to transverse the length of the plate. Essentially, each row would have ~55° C., ~72° C., and ~94° C. zones, and the lines would snake through these zones in a 'perpendicular'-directed fashion. An LoaC detector, based on a 96-well format, would have 24 different temperature zones (3 zones×8 rows). The optics of this system would be appropriately positioned above the microchannels to detect amplification.

The Diagnostic System (10) could also utilize a Detection System (36) designed for single molecule detection. Single molecule detection does not require amplification of the targeted analyte. Single molecules are detected by performing fluorescence excitation spectroscopy, with special attention paid to spatial and spectral selection, high quality optics and very sensitive detectors.

Data Acquisition—The Detection System (36) of the Diagnostic System (10) is designed to cycle and optically monitor the reaction mixtures (whether present or not) continuously, 24 hours a day, 7 days a week. Data is collected in column or row format; following the direction of the lines/tubes traversing the thermal-cycler. Data is collected once the entire train is fully parked within the Detection System (36), and stops when the appropriate number of data points has been collected.

The Diagnostic System (10) utilizes an optical detection system (36) to monitor the progress of the genetic amplification assays. Real-time reactions utilize fluorescence spectroscopy to distinguish different reporters within a single sample. Current technology permits the simultaneous detection of five different fluorescent reporters within one sample (e.g. Cyan 500, 6FAM, VIC, LC RED 610, and LC RED 670, with emission peaks at 500, 533, 568, 610, and 670 nm, respectively), but this number may be improved in the future. Aside from fluorescent spectroscopy, the Detection System (36) could be engineered to perform UV spectrophotometry to measure absorbance (e.g. 260 nm, 280 nm, 320 nm, etc.) or engineered to measure increases in turbidity.

FIG. 5 illustrates the optical heating/cooling wafer (184) that would be inserted into a modified real-time thermal cycler to comprise the Detection System (36) within the Diagnostic System (10). The optical heating/cooling wafer includes the following components:

28-1 Line
28-2 Line
28-3 Line
28-4 Line
28-5 Line
28-6 Line
28-7 Line
28-8 Line
28-9 Line
28-10 Line
28-11 Line
28-12 Line
29- Hole/Window exposing inner tubing (96 implied)
184- Optical Heating/Cooling Wafer Assays Performed by Diagnostic System—The Diagnostic System (10) is designed to be able to detect a wide range of different genetic assays, including all the assays described below. Genetic amplification can generally be divided into polymerase chain reaction (PCR)-based assays and isothermal amplification assays, both of which can be performed by the Diagnostic System (10). PCR-based assays involve cycling the mixture through different temperatures, either by heating a stationary mixture or by moving a mixture into different heating zones (e.g. Lab-on-a-Chip). Commonly used PCR parameters include 94° C., 55° C. and 72° C. Often, reverse transcription (RT) precedes PCR amplification, and these assays are referred to as RT-PCR assays. In contrast, isothermal amplification assays utilize one stable temperature to achieve nucleic acid amplification. Common temperatures for isothermal amplification are around 62-65° C.

There are many different ways to optically monitor PCR, RT-PCR, and isothermal amplification reactions. "Real-time" assays can be monitored as they progress, rather than endpoint assays, which need additional processing after amplification is completed to determine whether amplification occurred. A common "real-time" assay utilizes unlabeled forward and reverse primers with a probe labeled with a fluorescent reporter and a quencher. Many different variations of 'real-time' molecular reagents are available that have slightly altered chemistries, but achieve the same result. Each of these chemistries may be used in the described Diagnostic System (10). For the purpose of this document 'real-time' assays refer to all Taqman®-like assays and their variations, including those that use Locked Nucleic Acid (LNA) substituted Taqman® probes, molecular beacons, fluorescence resonance energy transfer (FRET) Probes, Scorpions® primers or probes, Plexor™ Technology, Light Upon eXtension (LUX™) primers, MethyLight Taqman®) Assays, and the like. After amplification, many of these probes allow for melting curve analysis, which can also be performed by the Diagnostic System (10). In addition to these sequence-specific detection assays, there are non-sequence specific double stranded DNA-binding dyes, such as SYBR® Green, which can be used to monitor amplification, but these dyes can not be used in multiplex analysis.

As previously mentioned, isothermal reactions can be performed and detected by the Diagnostic System (10). These assays include: Rolling Circle Amplification (RCA), Rolling Circle Chain Reaction (RCCR), Exponential Amplification Reaction (EXPAR), NEAR and NEA assays (Ionian Technologies), reverse transcription—loop mediated isothermal amplification (RT-LAMP) assays, Smart Amplification Process Version 2 (SMAP-2), and Nucleic Acid Sequence Based Amplification (NASBA®) assays. Many of these assays are monitored using SYBR® green or by evaluating changes in turbidity, but some work with molecular beacon style probes which permit multiplexing.

Figure 6:
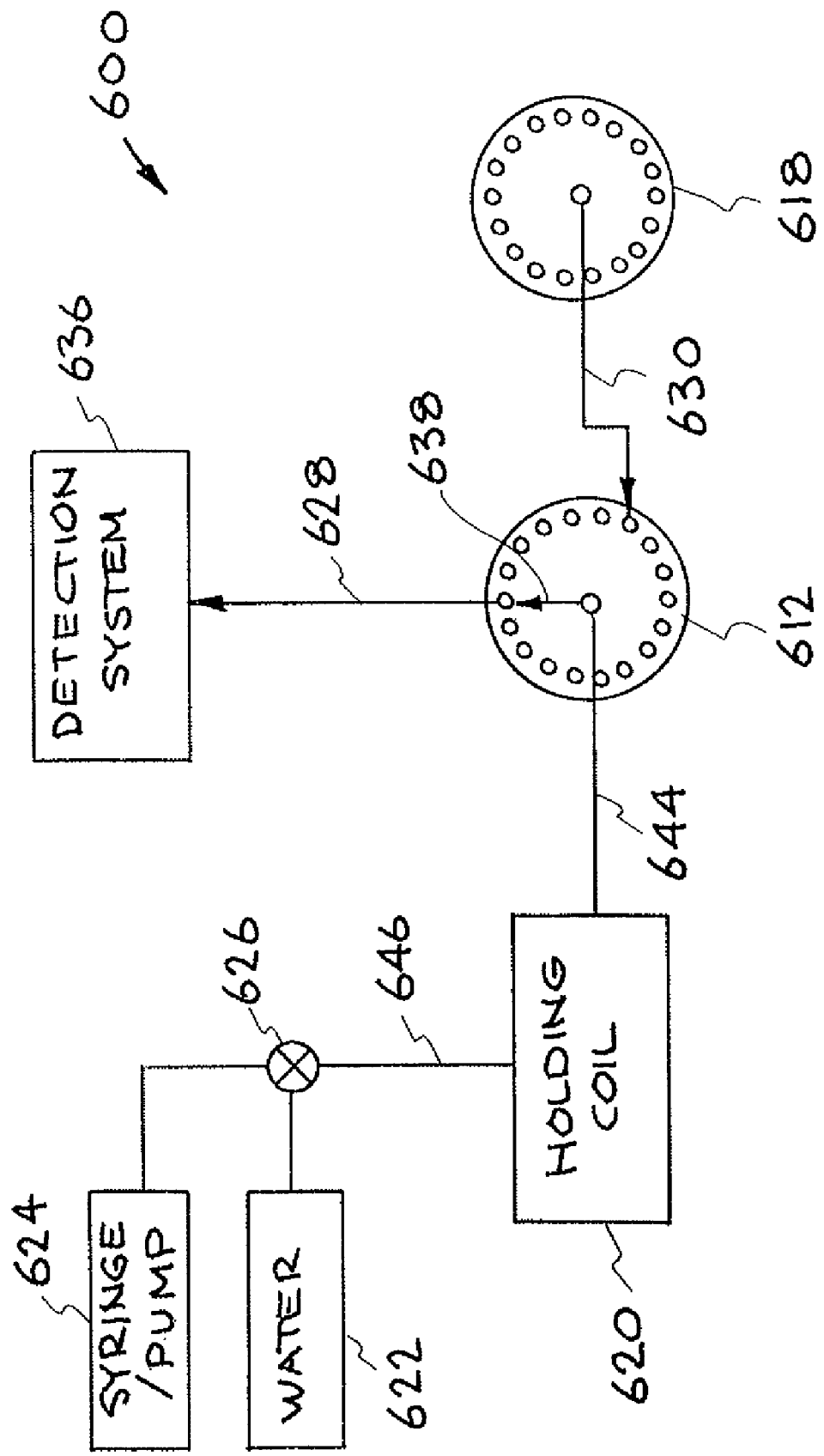
FIG. 6 illustrates another embodiment of the present invention.
Figure 7:
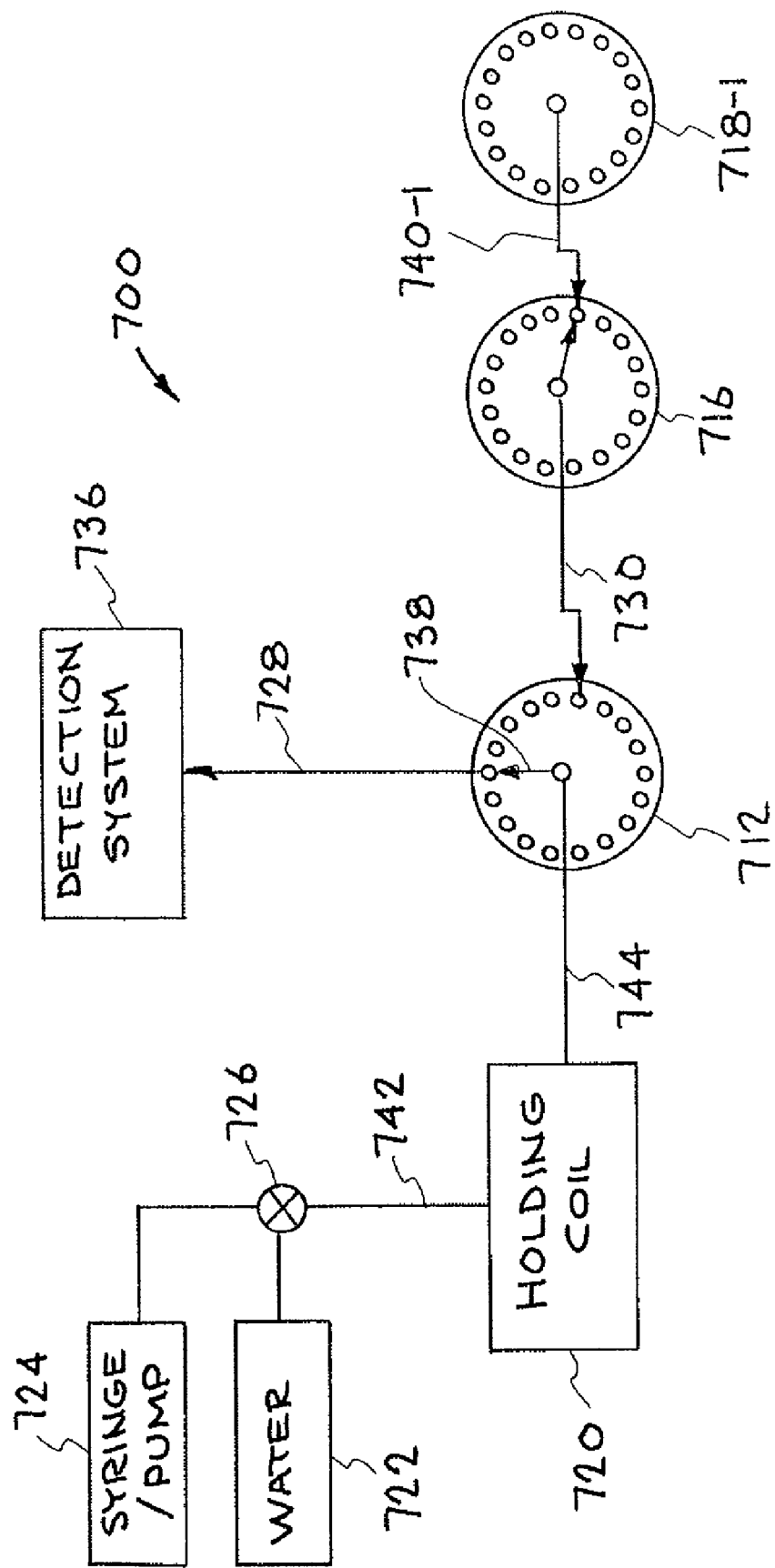
FIG. 7 illustrates another embodiment of the present invention.
Figure 8:
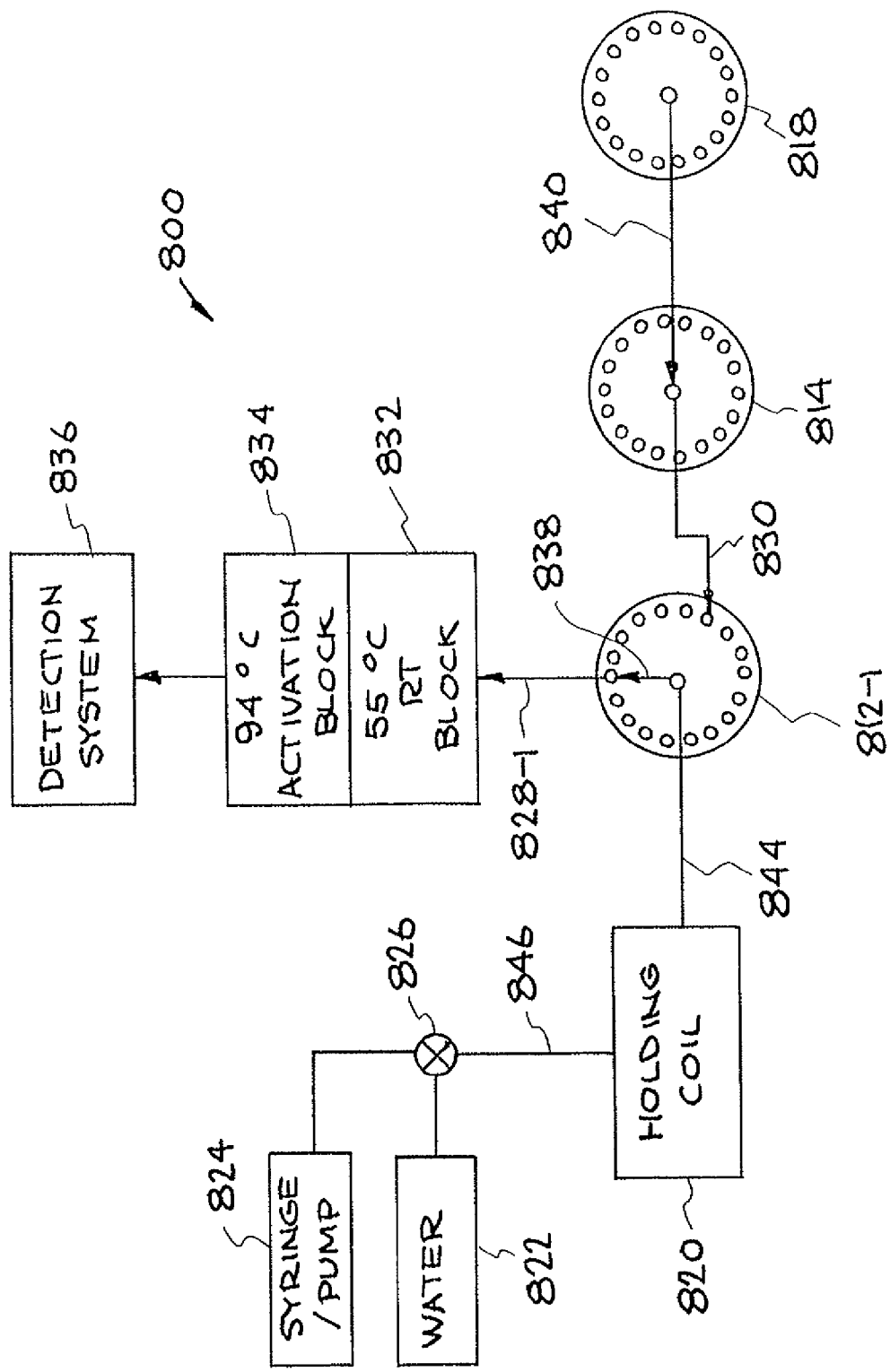
FIG. 8 illustrates yet another embodiment of the present invention.

FIG. 6: An alternative embodiment of the Diagnostic System (600) utilizes the same principles as the preferred embodiment (10), but lacks a Master Sample Valve (14), Master Reagent Valve (16), RT Block (32), and an Activation Block (34). The exclusion of these items allows the Diagnostic System (600) to only process samples in a serial manner against just one multiplex reagent panel (assuming daisy chained reagent valves are not included), rather than processing multiple samples in a parallel manner against a wide range of multiplex reagent panels. This alternative embodiment of a Diagnostic System (600) includes the following components:

612- Sample Valve
  618- Reagent Valve
  620- Holding Coil
  622- Water
  624- Syringe Pump
  628- Line
  626- Valve
  630- Line
  636- Detection System
  638- Valve Position Arrow
  644- Line
  646- Line FIG. 7: An alternative embodiment of the Diagnostic System (700) utilizes the same principles as the preferred embodiment (10), but lacks a Master Sample Valve (14), RT Block (32), and an Activation Block (34). The exclusion of these items allows the Diagnostic System (700) to only process samples in a serial manner against multiple reagent panels, rather than processing multiple samples in a parallel and asynchronous manner against a multiple multiplex reagent panels. This alternative embodiment of a Detection System (700) includes the following components;

712- Sample Valve
  716- Master Reagent Valve
  718-1 Reagent Valve
  720- Holding Coil
  722- Water
  724- Syringe Pump
  728- Line
  726- Valve
  730- Line
  736- Detection System
  738- Valve Position Arrow
  740-1 Line
  744- Line
  746- Line FIG. 8: An alternative embodiment of the Diagnostic System (800) utilizes the same principles as the preferred embodiment (10), but lacks a Master Reagent Valve (16). The exclusion of the Master Reagent valve allows the Diagnostic System (800) to process multiple samples in a parallel and asynchronous manner against just one multiplex reagent panel (assuming daisy chained reagent valves are not included), rather than processing multiple samples in a parallel and asynchronous manner against a multiple multiplex reagent panels. This alternative embodiment of a Detection System includes the following components:

812-1 Sample Valve
  814- Master Sample Valve
  818 Reagent Valve
  820- Holding Coil
  822- Water
  824- Syringe Pump
  828-1 Line
  826- Valve
  830-1 Line
  832- ~55° C. Reverse Transcription Block (RT Block)
  834- ~94° C. Activation Block (Activ. Block)
  836- Detection System
  838- Valve Position Arrow
  840 Line
  844- Line
  846- Line While the invention may be susceptible to various modifications and alternative forms, specific embodiments have been shown by way of example in the drawings and have been described in detail herein. However, it should be understood that the invention is not intended to be limited to the particular forms disclosed, Rather, the invention is to cover all modifications, equivalents, and alternatives falling within the spirit and scope of the invention as defined by the following appended claims.

Operation of the Diagnostic System (10)—The operation of the preferred embodiment of the Diagnostic System (10), as illustrated in FIG. 1A-G, FIG. 2-5, provides a method of detecting sequences in a sample. A flow channel is provided. A series of reagent plugs are formed in the flow channel. Sample preparation fluids are associated with the sample. The sample is associated with the reagent plugs forming sample-reagent plugs. In some embodiments the sample-reagent plugs are thermal-cycled to amplify the sample. Other embodiments achieve amplification under isothermal conditions and others do not require amplification. The sequences in the sample/sample-reagent plugs are detected using optical detection. The operation of the Diagnostic System (10) is controlled by a computer that runs a software code composed of step-types and in-line commands that direct the movements and operation of different system components. The system is fully automated and requires little hands-on time to initiate sample processing and screening. The Diagnostic System (10) asynchronously processes and screens samples in a parallel fashion. In other words, it is capable of initiating the processing of sample 'A' to be screened against pathogen panel 'V', and approximately two minutes later can begin processing sample 'B' to be screened against pathogen panel 'W'. This pattern (samples C, D, E . . . and pathogen panels X, Y, Z . . . ) can continue until all channels of the instrument become occupied. Different samples may be screened against the same or different pathogen panels. The timing between initiating subsequent samples may be varied, and the processing of each sample occurs independent of the other samples on the system. Each sample placed on the instrument is completed within a time frame similar to the other samples, and results for each sample become available in the order the samples were originally placed on the system.

The basic principle behind the operation of the Diagnostic System (10) is to extract, concentrate, and purify the genetic material from a sample matrix (e.g. blood, serum, buffy coat (leukocyte fraction of blood), feces, urine, cerebral spinal fluid, semen, genital secretions, pus, saliva, suspected cancer biopsy, cheek swab, tissues, cells, tears, perspiration, etc.), and to introduce this clean genetic material into multiple distinct genetic reactions that are optically monitored for the presence of different genetic sequences. The operation of the instrument can be divided into five main stages including: 1) nucleic acid extraction, concentration, and purification, 2) Sample Master Mix preparation, 3) assembly of a train of multiplexed reagent boxcars, 4) insertion of Sample Master Mix into reagent boxcars, 5) amplification and detection of completed multiplexed reactions, and 6) decontamination. Each of these steps is detailed below.

(1) Nucleic acid extraction, concentration, and purification—The Diagnostic System (10) is capable of processing multiple complex matrices for many different genetic sequences (also referred to as targets, markers, or analytes). The complex matrices may be derived from human or animals sources (e.g. blood, serum, buffy coat (leukocyte fraction of blood), feces, vomit, gastro-intestinal fluid, urine, cerebral spinal fluid, semen, genital secretions, pus, saliva, suspected cancer biopsy, cheek swab, tissues, cells, tears, perspiration, etc.), as well as from the environment (e.g. municipal water, waste water, lake water, surface swipes, soil and air samples, plant material, etc.). Each of these matrices is different and must be processed in a different manner in order to optimize the isolation of the desired genetic material. To achieve this broad-spectrum capability, the Diagnostic System (10) is able to utilize different multi-barrel nucleic acid extraction cartridges (62) that have been tailored to process different complex matrices to achieve optimal nucleic acid extraction and purification. Likewise, the Diagnostic System (10) can perform different fluidic protocols to optimize the performance of different multi-barrel nucleic acid extraction cartridges.

The Diagnostic System (10) draws a sample 1 (48-1) through line (94), which passes through sonication 1 chamber (80), where the sample may be subject to ultrasonic vibration to help dissociate the matrix, which may contain large particulate matter, clumps of cells, or mucus-like material. The extent of sonication depends on the application. In some circumstances it may be acceptable to lyse the sample by sonication, and in others, it may be preferable to slightly disrupt or agitate the sample to minimize the chances of large particulate matter clogging the system. The amount of sample 1 (48-1) drawn into line (94) depends on the matrix processed and the expected titer of the suspected pathogens being screened. To screen for low titer pathogens, it may be necessary to draw up several milliliters of sample (e.g. blood) and have the sample filtered and concentrated prior to lysis within the multi-barrel cartridge (62). Alternatively, for high titer pathogens, smaller volumes may be processed (e.g. <100 µL), for which filtering may not be necessary. In these circumstances, sample 1 (48-1) may be directly mixed with a lysis buffer.

The Diagnostic System (10) is equipped to hold multiple lysis buffers. The types of lysis and nucleic acid extraction and purification possible by the Diagnostic System (10) are generally covered under U.S. Pat. No. 5,234,809, European Patent No. 0,389,063, and equivalents in other countries. The preferred protocol for extracting and purifying nucleic acids depends on whether the intended genetic target(s) is RNA, DNA, or both, and the type of the matrix being processed.

One manner in which the Diagnostic System (10) may perform nucleic acid extraction and purification is described here. The system partially draws sample 1 (48-1) (FIG. 1B) through the sample line (94) and into the sample valve 1 (12-1), at which point the rotor of the multi-position valve turns to pick up a lysis buffer (70 or 71) that is specific to the application, before returning to the sample line (94) to draw more sample into holding coil 1 (20). Depending on the amount of sample processed, the valve's rotor may alternate back and forth between line (94) and line (90) or (73) under near-continuous suction from the syringe pump (24) to intersperse the lysis buffer with sample 1. The sample and lysis buffer mixture are now partitioned within the holding coil 1 (20) and line (44) are pushed into line (110) to enter the mixing lysis chamber 1 (58). The lysis mixing chamber 1 (58) is made of several linear chambers of different inner diameter distance. The pushing and pulling of the sample 1/lysis mixture through these chambers encourages turbulent fluid flow and causes the thorough mixing. At this point, the mixture is incubated to allow the lysis buffer to rupture proteinaceous, lipid, and carbohydrate-based membranes and liberate the previously protected genetic material. The lysed sample mixture is now composed of insoluble material (e.g. cell and nuclear membranes, cytoskeletons, extra-cellular matrices like mucus and particulate matter) and soluble material (DNA, RNA, proteins, lipids, etc.), but the separation of components between these two fractions is not complete.

The lysed sample mixture is drawn into the holding coil 1 (20) and sent into line (119), which passes through sonication chamber 2 (82) for additional mechanical disruption. The solution is then pushed through the left side (132) of the multi-barrel nucleic acid extraction cartridge (62)(FIG. 1B & FIG. 3), which contains filters (138 & 136) to trap the insoluble material. The soluble material passes through the left side of the cartridge (132) and is delivered past junction (74), which is a four-way open valve, and into line (75). Once in line (75), the direction of the syringe pump (24) is reversed, and rotor of sample valve 1 (12-1) is turned to line (118). The soluble mixture is then retrieved back down into the right side (134) of the multi-barrel cartridge (62), which contains a silica pack (140). The soluble DNA and RNA binds to the silica pack, whereas the soluble proteins and lipids pass through the silica pack (140). Once the soluble material has fully passed through the silica pack, the pump (24) is reversed again and the remaining solution is pushed back through the silica pack (140), past junction (74), through line (75), and into Master Waste 1 (210) (presuming the lysis buffer contains guanidine salts, which can not be mixed with bleach) (FIG. 2).

Once the nucleic acid from lysed sample 1 (48-1) is bound to the silica pack (140)(FIG. 1B & FIG. 3), the syringe pump (24) draws 70% ethanol (54) through line (96) and into holding coil 1 (20). The pump is reversed and the 70% ethanol is delivered through line (118) and to Master Waste 1 (210) (FIG. 2). This washes the bound nucleic acid of contaminants that may inhibit subsequent catalytic and enzymatic reactions. The syringe pump draws air (64) into holding coil 1 and expels it through line (118) to dry the bound nucleic acid. The pumping of air over the silica pack may occur multiple times to effectively achieve 'drying'.

The pump (24) then draws buffer 1 (66) (elution buffer, e.g. 10 mM Tris, pH 7.5)(FIG. 1B & FIG. 3) into the holding coil 1 (20) and sends it through line (118) and over the silica pack (140). The nucleic acid is eluted from the silica pack and is solubilized within the elution buffer. Concentrating the sample's nucleic acid can be achieved by eluting the nucleic acid in a volume smaller than the originally processed sample. After the entire volume of elution buffer is pushed into line (118), it is followed by air (64) to prevent the eluted sample from mixing with carrier fluid (e.g. water (22)). The eluted material is positioned in line (75) and holding coil 2(76)(FIG. 2). Line (112) is activated and the syringe pump (24) draws the eluted sample into the elution mixing chamber (60)(FIG. 1A). The eluted material is pushed back and forth between the alternating small and large diameter tubing Within the elution chamber to thoroughly mix the eluted material to achieve homogeneity. This is necessary, since the nucleic acid eluted from the silica pack is more concentrated in the portion of elution buffer that first passed through the silica pack than the last portion; and mixing a concentration gradient within a long thin line does not happen quickly without a mixing chamber.

It is generally possible to enrich for RNA, DNA or both by choosing a multi-barrel nucleic acid extraction cartridge that contains nucleic acid binding material that is specific to the targeted genetic material and using the appropriate protocol and buffers (lysis and washing) to optimize the collection of the desired material. In addition, it is possible to perform enzymatic reactions on the binding material, including specific nucleic acid digestions (e.g. DNase and RNase) to further process the sample prior to downstream processing. Similar sample manipulations may occur earlier in sample preparation, including proteinase K digestion.

2) Sample Master Mix preparation—The Diagnostic System (10) can perform many types of reactions, each of which require unique reagents. These reactions include all genetic-based detection assays, whether or not nucleic acid amplification occurs. In theory, single molecule detection, which does not require amplification of the original template, could be performed on the Diagnostic System. The use of assays that require nucleic acid amplification is more likely and includes those performed at one temperature (isothermal amplification) and those requiring thermal-cycling (polymerase chain reaction).

A real-time RT-PCR assay is used here as an example of a typical assay performed by the Diagnostic System (10). However, this assay should not be considered the only assay that can be performed by this system.

The Diagnostic System (10) assembles a Sample Master Mix that includes some of the extracted, concentrated, and purified nucleic acids, and some 2x reaction buffer and enzyme mix, Real-time RT-PCR reactions can utilize either a traditional 2x reaction buffers, which includes dNTPs, or customized reaction buffers that contain deoxyuridine triphosphates rather than deoxythimidine triphosphates. Uracil-containing 2x reaction buffers are often used in re-usable flow-through systems, since Uracil DNA glycosylase (UDG) can be used in each reaction to digest uracil-containing PCR products, which minimizes the chances of previously amplified products from causing false positives in subsequent reactions. This chemistry will be further detailed in section 6, which explains the decontamination of the system.

To create the Sample Master Mix, the syringe pump (24) (FIG. 1B) draws air (64) into the holding coil 1 (20), followed by 2x reaction buffer (52), enzymes (50), and purified nucleic acid that has been positioned in line (112). The proportions of these fluids are consistent with proportions normally used for the designated assay. For this example, the enzyme mix includes taq polymerase, reverse transcriptase (RT), and Uracil DNA Glycosylase (UDG). The Sample Master Mix, flanked by air gaps, is delivered to line (106) and the Master Mixing Chamber 3 (56); where it is pumped back and forth through tubing of alternating small and large diameters to thoroughly mix the solution.

3) Assembly of a train of multiplex reagent boxcars—A train of multiplex reagent boxcars (FIG. 10) is formed from reagent valve 1 (18-1) while the sample valve 1 (12-1) is in the process of extracting the nucleic acids from sample 1 (48-1) and forming the Sample Master Mix. The train of multiplex reagent boxcars is an analogy used to describe the assembly of several distinct multiplex reagents mixtures organized within a single line. Each boxcar in the train represents different reagent mixture (FIG. 1E, 168, 170, 172, 174, 176, 178, 180, and 182). The boxcars are kept separate within the lines of the system by either oil (78) or air (64); and are transported through the system along different lines, similar to the way a locomotive train moves along railroad tracks. Each boxcar contains a multiplex mixture of analyte specific reagents (e.g. primers, probes, etc.).

Prior to assembling the train, all the reagent mixtures (168, 170, 172, 174, 176, 178, 180, and 182) and oil (78) are primed up to the multi-position reagent valve 1 (18-1)(FIG. 1E & FIG. 4). The syringe pump (24)(FIG. 1B) draws an oil (78) (FIG. 1E) into line (40-1) followed by alternating between different reagent mixtures and oil until the number of reagent mixtures equals the number of optical windows available in the detection system (36). For this example, there are eight different reagent mixtures that are part of the train. Oil precedes and succeeds every reagent mixture, ensuring no mixing between reagent mixtures or the carrier fluid (e.g. water (22)) occurs. After the last oil plug is drawn into line (40-1), the rotor turns toward line (164) and water is drawn into the line to follow the train, as the train passes through the Master Reagent valve (16), line (42), the Master Sample valve (14), and into line (30-1)(FIG. 1A).

For the Respiratory Pathogen Panel example (FIG. 1F and FIG. 4)) used here, the reaction mixtures are 3-plex mixtures. The probes of each mixture are labeled with Cyan 500, VIC, and LC RED 670 reporter molecules with the appropriate quenchers. The controls and targets have been described earlier and are oriented within the eight boxcars as follows: 1) buffer only positive and negative controls, 2) PSA, RSV, Adeno B, 3) 115, Para 1, PCR-I, 4) PSA, Para 3, Adeno C, 5) H3, MPV, PCR-I, 6) PSA, RhV, Adeno E, 7) H1, CoV, PCR-I, and 8) PSA, Pan Flu A, and Flu B.

Trains can be assembled from any of the reagent valves (18-1, 18-2, 18-3, 18-4, 18-5 . . . 18-17)(FIG. 1D) or from the unlimited number of daisy-chained reagent valves (19-1 through 19-17, 20-1 through 20-17, 21-1 through 21-17, and n-1 through n-17) (FIG. 1F). This configuration enables the Diagnostic System (10) to hold an unlimited number of reagents. As previously mentioned the Diagnostic System (10) is capable of storing a common set of reagents that are provided to multiple samples being processed in an asynchronous and parallel fashion. The train of multiplex reaction mixtures that was assembled in line (40-1) can be delivered to any desired channel within the instrument (i.e. any one of the 12 samples being processed around the sample valves (12)). The train can be diverted to any channel when it enters the central port of the Master Sample valve (14), which has the option of delivering the train to any of the desired sample valves (12-1, 12-2, 12-3, 12-4, 12-5 . . . 12-18) (FIG. 1C). A Master Sample valve (14) with more ports would allow more than 18 sample valves (12) to be part of the Diagnostic System (10).

4) Insertion of Sample Master Mix into reagent boxcars—For this example, the Master Sample valve (14)(FIG. 1A) directs the train into line (30-1) towards sample valve 1 (12-1). The first reaction mixture (168)(FIG. 1G) within the train reaches sample valve 1 (12-1)(FIG. 1B) and stops halfway into the valve. The valve's rotor turns to line (106)(FIG. 1B) and pulls in an aliquot of the Master Sample Mix that has been previously prepared. The valve's rotor returns to line (30-1) to draw in the rest of the first reaction mixture, the intervening oil plug, and half of the next reagent mixture, before stopping and drawing in another aliquot of Master Sample Mix. This process continues until master sample mix has been equally added to each of the eight boxcars in the train. The train in now positioned in the line (44) and holding coil 1 (20). The sample valve's (12-1) rotor turns to line (28-1), where the rotor's valve position arrow (38) is pointed in FIG. 1B, and pushes the completed reaction mixture train into line (28-1).

5) Amplification and detection of the train of completed multiplex reactions—Line (28-1)(FIG. 1A) runs through the 55° C. RT Block (32), the 94° C. Activation Block (34), and the Detector System (36), which are heated and thermal-cycling elements. To prevent the unintended small movement of the train in line (28-1), the rotors of sample valve 1 (12-1) and the waste valve (216)(FIG. 2) are turned away from line (28-1) while the train is stationary. Closing the line prevents unintended movement that may be caused by the heating and cooling of fluids within this line.

Once the train is in line (28-1)(FIG. 1A), it stops prior to reaching the RT Block (32) to incubate at room temperature. This room temperature incubation period allows the heat-labile Uracil DNA Glycosylase (UDG) time to digest any product remaining from the previously processed sample, which may have survived the previous bleach decontamination procedure. The choice to include UDG in these reactions is dependent on the level of concern for previously amplified product working its way down line (28-1) and into sample valve 1 (12-1), which potentially could cause an aberrant false positive. This should not occur, since amplified product should only be produced in the 55° C. RT Block (32), 94° C. Activation Block (34), and especially in the Detection System (36); and these products are never pulled down into sample valve 1 (12-1) where amplified nucleic acid is more likely to escape the bleach treatment. Furthermore, the fluid flow through line (28-1) is directional and always goes toward the waste valve (216). An exception to this rule is if the Detection System (36) carries out Lab-on-a-Chip style amplification, which requires minor back-and-forth movement of the train through different heating zones to achieve amplification, but this movement is not sufficiently large to bring amplified product near sample valve 1 (12-1). The directional flow of lines (28-1 through 28-12)(FIG. 1C) protects against amplified product contaminating the sample valves (12-1, 12-2, etc.). However, despite these precautions, Brownian motion may cause amplified product, which survived the bleaching protocol, to migrate down into a sample valve (12), potentially causing a false positive.

After the train completes the UDG incubation step, the train is pushed into the 55° C. RT Block (32)(FIG. 1A) where heat-labile UDG is inactivated and each of the reaction mixtures is placed at 55° C. to allow RNA targets to be reverse transcribed (assuming some of the targets are RNA based). The length of the RT incubation time varies depending on the size of the target EDNA generated, but generally can be completed in less than 10 minutes. After RT, the train is delivered to the 94° C. Activation Block (34), where the train remains for approximately 2 minutes to ensure full activation of the taq polymerase. Different enzymes have different activation requirements. After activation, the train proceeds to the Detection System (36) for amplification and optical monitoring. Upon completion of the determined number of cycles, the train is pushed through the waste valve (216) and into Master Waste 2 (212).

6) Decontamination—The Diagnostic System's (10) waste system (200) is illustrated in FIG. 2. All of the reagents and solutions that enter the lines of this flow-through system are eventually delivered to a waste receptacle. The Diagnostic System (10) can be roughly divided into sterile and non-sterile halves. The sterile half never comes in contact with patient sample and includes the reagent valves (18-1, 18-2, etc.)(FIG. 1D), daisy-chained reagent valves (19-1, 20-1, 21-1, n-1)(FIG. 1F), Master Reagent valve (16)(FIG. 1A), and Master Sample valve (14)(FIG. 1A). Because sample never enters these valves, it is not necessary to thoroughly decontaminate these valves and lines between processing different samples. In contrast, the sample valves (12-1, 12-2, etc.)(FIGS. 1A, 1B, & 1C) and the lines connecting these valves to waste valve (216)(FIG. 2), Master Waste 1 (210), Master Waste 2 (212), multi-barrel nucleic acid extraction cartridge (62)(FIG. 1B), elution mixing chamber 2 (60), mixing lysing chamber 1 (58), Master mixing chamber 3 (56), RT Block (32)(FIG. 1A), Activation Block (34), and Detection System (36), are all exposed to sample during processing and must be thoroughly decontaminated between processing different samples.

Bleach Treatment—Bleach (68) (1.3% sodium hypochlorite or the equivalent to 20% house-hold bleach) effectively cleanses the systems lines and valves, leaving them free of residual nucleic acid that would otherwise cause carry-over contamination for subsequent samples. The bleach is ultimately delivered to Master Waste 2 (212)(FIG. 2), whereas Master Waste 1 (210) accepts liquids containing guanidine-based salts. The separation of guanidine-based salts and bleach is essential to prevent the production of toxic gases, including hydrogen chloride (HCl) and hydrogen cyanide (HCN). Lines recently exposed to guanidine-based salt solutions are rinsed with water, before bleach is added to these lines. Bleach is generally pushed in a directional manner through the lines and directly to Master Waste 2 (212), however, this is not possible for lines 119, 118, 75, and 94 (FIG. 1B). These lines service the multi-barrel cartridge (62) where nucleic acid extraction occurs and where the sample 1 (48-1) enters the Diagnostic System (10). Bleach entering lines 19, 118, and 75 is delivered up to the holding coil 2 (76) (FIG. 2) and no further to prevent it from mixing with Waste System 1 (210), which contains waste including guanidine-based salts. After reaching holding coil 2 (76), the bleach is retrieved into holding coil 1 (20)(FIG. 1B), before being delivered through line 106 or 110 to Master Waste 2 (212). Line 94 must also be decontaminated in a bi-directional manner, including both the inside and outside of the line, which came in contact with sample 1 (48-1) during loading of the sample onto the instrument. To achieve thorough decontamination of this line, the Diagnostic System (10) prompts the operator to replace the sample vial with an empty vial at the start of initiating the run, after sample 1 (48-1) has been drawn into the system. The empty vial serves as a receptacle for bleach, which is pump both in and out to decontaminate the line, both inside and out at the terminus of the line. The terminus of line 94 can either be an open-ended tube or a needle-like structure that is connected to the sample line.

After bleaching the entire channel, the system is rinsed with water (22)(FIG. 1B), and may also be treated with buffer 2 (72) (e.g. a dilute solution of Tris Base, NaCl, and Triton X-100), which can serve as a conditioner to both neutralize the pH of the system and to treat the lines with a detergent to facilitate the flow of fluids through the lines of the system. An alcohol wash may also be passed through the lines to condition the tubing for smooth fluid flow.

Decontamination of the lines emanating from sample valve 1 (12-1)(FIG. 1B), except line 28-1, may occur as soon as the sample 1 (48-1) has been processed and is parked in the Detection System (36) for amplification and analysis. Line 28-1 may be cleaned last, once the assay is complete. Prior to delivering bleach (68) through the lines that have been exposed to sample; the used multi-barrel nucleic acid extraction cartridge (62) is replaced with a similar 'cleaning' cartridge that lacks the filters and silica pack. The disposal of the old cartridge, containing the captured insoluble sample material, removes this material from the system before bleach has the opportunity to spread it through the system, potentially fouling the lines and valves.

UDG Treatment—Uracil-containing products are generated when the 2× reaction buffer (52) contains deoxyuridine triphosphates rather than deoxythimidine triphosphates. During PCR cycling, the deoxyuridine triphosphates are incorporated into amplified product. After amplification and analysis, these products are delivered directly to Master Waste 2 (212)(FIG. 2) and the line (28)(FIG. 1A) running through the components where amplification occurred are treated with bleach. Bleach should eliminate all products from the previous run. However, should some product escape the bleach treatment, the presence of uracils in the sugar-phosphate backbone make these products susceptible to Uracil DNA Glycosylase (UDG) digestion. To include this extra safety measure, the Diagnostic System can be programmed to perform a UDG incubation step at the start of every new reaction. The precautionary room temperature UDG incubation step occurs just prior to reverse transcription in line (28). The 55° C. reverse transcription step inactivates the heat-labile UDG and prevents it from digesting the products of the current reaction.

Bottlenecks of Asynchronous System—Although the system is asynchronous and can process multiple samples simultaneously in a parallel fashion, each channel of the system must share certain components of the system. The sharing of these components can be considered bottleneck areas. One such area is line (42)(FIG. 1A), since all the reagents stored off the reagent valves (18-1, 18-2, etc.)(FIG. 1D) must be delivered through this line to reach the Master Sample valve (14)(FIG. 1A) where it is directed to one of the sample valves (12-1, 12-2, etc.)(FIG. 1C). The time required to assemble the train of reagent boxcars and deliver it to the appropriate sample valve (12) is small (approximately 2-3 minutes). The short occupancy time of this bottleneck does not adversely delay the processing of multiple samples, since roughly the same amount of time is required to initiate the processing of each sample (e.g. entering medical record information and requesting a particular assay to be performed).

Another component of the Diagnostic System (10) that is shared amongst the multiple channels of the instrument is the waste valve (216)(FIG. 2). The waste valve (216) must be open for the brief amount of time it takes to transport the completed reaction train into line (28)(FIG. 1A) and to the 55° C. RT block (32), 94° C. Activation Block (34), and Detection System (36). While the reaction train is 'parked' in these locations, the rotors in waste valve 1 (216)(FIG. 2) and the connected sample valves (12-1, 12-2, etc.)(FIG. 1C) are turned to a closed position, to prevent the unintended movement of the train while it undergoes incubations at room temperature, 55° C., 940° C., or thermal-cycling. The waste valve only allows one channel of the instrument to move completed reaction mixtures through one of the many lines entering the detection system (36)(FIG. 5) at a time. The high demand on this valve can be easily remedied by adding two or more waste valves to the system. For example, if an instrument were to be constructed with two waste valves, these waste valves would each service six of the 12 lines entering a 12 channel instrument, rather than all 12, thereby reducing this bottleneck. The addition of an extra waste valve is not necessary, but does largely eliminate this bottleneck, and prevents the processing of one sample from delaying the processing of another sample.

The invention claimed is:

1. An instrument for detecting different genetic sequences in a sample, comprising:
    flow channels;
    an optical detector for monitoring said flow channels, said optical detector having a multiplicity of optical windows;
    a nucleic acid extraction cartridge operably connected to said flow channels;
    a sample source;
    sources of sample preparation fluids and reagent fluids and decontaminating fluids;
    a pump operatively connected to said flow channels, to said nucleic acid extraction cartridge, to said sample source and said sources of sample preparation fluids and reagent fluids and decontaminating fluids;
    a sample multi-position valve for receiving and processing the sample, said sample multi-position valve connected to flow channels, to said optical detector, to said nucleic acid extraction cartridge, to said sample source, and to said sources of sample preparation fluids and reagent fluids and decontaminating fluids;
    a reagent multi-position valve operatively connected to said flow channels, to said reagent fluids, and to said sample multi-position valve;
    two separate waste receptacles for receiving, via said flow channels, chemically incompatible fluids used in said nucleic acid extraction cartridge and the decontaminating of the system; and
    a control that coordinates the actions of the valves, pumps, and the optical detector, assemble genetic assays using the nucleic acids purified from a sample, transport the genetic assays to the optical detector for amplification and fluorescent analysis, report on the results, and deliver decontaminating fluids through the system after each sample is processed;
    wherein said sample multi-position valve for receiving and processing a sample utilizes said nucleic acid extraction cartridge creates a sample master mix comprised of the nucleic acids purified from a sample, polymerases, and 2× reaction buffer;

wherein said reagent multi-position valve assembles within said flow channel a series of multiplex reagent mixtures containing primers, probes, and controls;

wherein said sample multi-position valve for receiving and processing a sample associates portions of a sample master mix with some of the multiplex reagent mixtures in the series to generate a series of multiplex reaction mixtures containing all the necessary components for genetic amplification within said flow channel for the sample being processed; and wherein the series of multiplex reaction mixtures containing all the necessary components for genetic amplification are transported to said optical detector in said flow channel, in operative position to the multiplicity of optical windows, for genetic amplification and fluorescent analysis.

2. The instrument for detecting different genetic sequences in a sample of claim 1 further comprising a flow-through sonicator, an acoustic focusing element, and a sequestering cell for retaining particles or beads operably connected to said nucleic acid extraction cartridge.

3. The instrument for detecting different genetic sequences in a sample of claim 1 wherein said optical detector is a real-time isothermal or thermal-cycling analysis detector that contains a flow channel with a multiplicity of optical windows.

4. The instrument for detecting different genetic sequences in a sample of claim 1 including rotary valves wherein said optical detector passes through said rotary valves that are operatively associated with said flow channel entering and leaving the optical detector, and these valves can be rotated to prevent fluid flow or movement during genetic amplification and fluorescent analysis.

5. The instrument for detecting different genetic sequences in a sample of claim 1 wherein said sources of sample preparation fluids and reagent fluids and decontaminating fluids include wash and conditioning buffers, enzymes, air, fluorescent probes, fluorescent primers, and/or fluorescent dyes.

6. The instrument for detecting different genetic sequences in a sample of claim 1 wherein said optical detector includes a light source directed into the sample and a light detector.

7. The instrument for detecting different genetic sequences in a sample of claim 1 wherein said nucleic acid extraction cartridge is a multi-barrel nucleic acid extraction cartridge that contains a filter and/or a silica pack located inside in one or more barrels.

8. An instrument for simultaneously detecting different genetic sequences in multiple samples in an asynchronous manner comprising:
flow channels;
an optical detector with a multiplicity of optical windows for monitoring multiple flow channels;
one or more heated elements held at constant temperature and operatively connected to said optical detector;
a nucleic acid extraction cartridge operably connected to said flow channels;
sample sources;
sources of sample preparation fluids and reagent fluids and decontaminating fluids;
pumps operatively connected via said flow channels to said sample sources and said sources of preparation fluids and reagent fluids and decontaminating fluids and said nucleic acid extraction cartridge;
sample multi-position valves for receiving and processing samples, said flow channels connect said sample multi-position valves to said optical detector, to said one or more heated elements held at constant temperature, to said nucleic acid extraction cartridge, to said sample sources, and to said sources of sample preparation fluids and reagent fluids and decontaminating fluids;
a master sample multi-position valve operatively connected via said flow channels to two or more said sample multi-position valves;
a reagent multi-position valve operatively connected via said flow channels to said sources of reagent fluids and to said master sample multi-position valve;
two separate waste receptacles for receiving, via said nucleic acid extraction cartridge and the decontaminating of the system; and
a control that coordinates the actions of the valves, pumps, and the optical detector, assemble genetic assays using the nucleic acids purified from the samples, transport the genetic assays to the one or more heated elements held at constant temperature and the optical detector for amplification and fluorescent analysis, report on the results, and deliver decontaminating fluids through the system after each sample is processed; wherein said sample multi-position valves for receiving and processing samples utilize said nucleic acid extraction cartridge and create multiple sample master mixes comprised of nucleic acids purified from the samples, polymerases, and 2× reaction buffer;
wherein said reagent multi-position valve assembles within said flow channel a series of multiplex reagent mixtures containing primers, probes, and controls;
wherein said master sample multi-position valve directs, through said flow channel, the series of multiplex reagent mixtures generated by said reagent multi-position valve, to any of said sample multi-position valves;
wherein said sample multi-position valves for receiving and processing samples associate portions of the sample master mixes with some of the multiplex reagent mixtures in the series to generate series of multiplex reaction mixtures containing all the necessary components for genetic amplification within said flow channels for each of the samples being processed;
wherein series of multiplex reaction mixtures containing all the necessary components for genetic amplification are transported through said flow channels to said one or more heated elements held a constant temperature and to said optical detector, in operative position to the multiplicity of optical windows, for genetic amplification and fluorescent analysis; and
wherein multiple series of multiplex reaction mixtures generated through the near simultaneous processing of multiple samples are delivered to the optical detector in an asynchronous manner where they undergo asynchronous genetic amplification and fluorescent analysis.

9. The instrument for simultaneously detecting different genetic sequences in multiple samples in an asynchronous manner of claim 8 further comprising flow-through sonicators operably connected to said nucleic acid extraction cartridge.

10. The instrument for simultaneously detecting different genetic sequences in multiple samples in an asynchronous manner of claim 8 wherein said optical detector is a real-time isothermal or thermal-cycling analysis detector that contains flow channels with a multiplicity of optical windows and is able to separately monitor each of the flow channels in an asynchronous manner.

11. The instrument for simultaneously detecting different genetic sequences in multiple samples in an asynchronous manner of claim 8 wherein said flow channels entering said optical detector pass through rotary valves that are operatively associated with said flow channels entering and leaving said optical detector, and these valves can be rotated to prevent fluid flow or movement during genetic amplification and fluorescent analysis.

12. The instrument for simultaneously detecting different genetic sequences in multiple samples in an asynchronous manner of claim 8 wherein said sources of sample preparation fluids and reagent fluids and decontaminating fluids include wash and conditioning buffers, enzymes, polymerases, lysis buffers, oil, bleach, air, control, fluorescent probes, fluorescent primers, and/or fluorescent dyes.

13. The instrument for simultaneously detecting different genetic sequences in multiple samples in an asynchronous manner of claim 8 wherein said one or more heated elements held at constant temperature allow for reverse transcription and full activation of the polymerases in the reaction mixtures.

14. The instrument for simultaneously detecting different genetic sequences in multiple samples in an asynchronous manner of claim 8 wherein said nucleic acid extraction cartridge is a multibarreled nucleic acid extraction cartridge that contains a filter and/or a silica pack located inside in one or more barrels.

15. An instrument for simultaneously detecting different genetic sequences in multiple samples in an asynchronous manner comprising:
   flow channels;
   an optical detector with a multiplicity of optical windows for monitoring said flow channels;
   one or more heated elements held at constant temperature and operatively connected to said optical detector;
   a nucleic acid extraction cartridge operably connected to said flow channels;
   sample sources;
   sources of sample preparation fluids and reagent fluids and decontaminating fluids;
   pumps operatively connected via said flow channels to said sample sources and said sources of preparation fluids and reagent fluids and decontaminating fluids and to said nucleic acid extraction cartridge;
   sample multi-position valves for receiving and processing samples, said flow channels connect said sample multi-position valves to said optical detector, to said one or more heated elements held at constant temperature, to said nucleic acid extraction cartridge, to said sample sources, and to said sources of sample preparation fluids and reagent fluids and decontaminating fluids;
   a master sample multi-position valve operatively connected via said flow channels to two or more sample multi-position valves;
   reagent multi-position valves operatively connected via said flow channels to said sources of reagent fluids;
   a master reagent multi-position valve operatively connected via said flow channels to two or more reagent multi-position valves and to the master sample multi-position valve;
   two separate waste receptacles for receiving, via said nucleic acid extraction cartridge and the decontaminating of the system; and
   a control that coordinates the actions of the valves, pumps, and the optical detector to assemble genetic assays using the nucleic acids purified from the samples, transport the genetic assays to the one or more heated elements held at constant temperature and the optical detector for amplification and fluorescent analysis, report on the results, and deliver decontaminating fluids through the system after each sample is processed wherein said sample multi-position valves for receiving and processing samples utilize said nucleic acid extraction cartridge and create multiple sample master mixes comprised of nucleic acids purified from the samples, polymerases, and 2× reaction buffer;
   wherein said reagent multi-position valves assemble within said flow channels series of multiplex reagent mixtures containing primers, probes, and controls;
   wherein said master reagent multi-position valve may be connected to multiple said reagent multi-position valves, including said reagent multi-position valves that are daisy-chained together, thereby allowing said sample multi-position valves access to an unlimited number of probes, primers, and controls;
   wherein said master reagent multi-position valve directs series of multiplex reagent mixtures generated by said reagent multi-position valves to said master sample multi-position valve via said flow channel;
   wherein said master sample multi-position valve directs, through said flow channels, series of multiplex reagent mixtures, generated by said reagent multi-position valves and passed through said master reagent multi-position valve, to any of said sample multi-position valves;
   wherein said sample multi-position valves for receiving and processing samples associate portions of the sample master mixes with some of the multiplex reagent mixtures in the series to generate series of multiplex reaction mixtures containing all the necessary components for genetic amplification within said flow channels for each of the samples being processed;
   wherein series of multiplex reaction mixtures containing all the necessary components for genetic amplification are transported through said flow channels to said one or more heated elements held a constant temperature and to said optical detector, in operative position to the multiplicity of optical windows, for genetic amplification and fluorescent analysis; and
   wherein multiple series of multiplex reaction mixtures generated through the near simultaneous processing of multiple samples are delivered to the optical detector in an asynchronous manner where they undergo asynchronous genetic amplification and fluorescent analysis.

16. The instrument for simultaneously detecting different genetic sequences in multiple samples in an asynchronous manner of claim 15 further comprising flow-through sonicators nucleic acid extraction cartridge.

17. The instrument for simultaneously detecting different genetic sequences in multiple samples in an asynchronous manner of claim 15 wherein said optical detector is a real-time isothermal or thermal-cycling analysis detector that contains a multiplicity of optical windows.

18. The instrument for simultaneously detecting different genetic sequences in multiple samples in an asynchronous manner of claim 15 wherein said flow channels entering said optical detector pass through rotary valves that are operatively associated with said flow channels entering and leaving said optical detector, and these valves can be rotated to prevent fluid flow or movement during genetic amplification and fluorescent analysis.

19. The instrument for simultaneously detecting different genetic sequences in multiple samples in an asynchronous manner of claim 15 wherein said sources of sample preparation fluids and reagent fluids and decontaminating fluids include wash and conditioning buffers, enzymes, polymerases, lysis buffers, oil, bleach, air, control, fluorescent probes, fluorescent primers, and/or fluorescent dyes.

20. The instrument for simultaneously detecting different genetic sequences in multiple samples in an asynchronous manner of claim 15 wherein one or more heated elements held at constant temperature allow for reverse transcription and full activation of the polymerases in the reaction mixtures.

21. The instrument for simultaneously detecting different genetic sequences in multiple samples in an asynchronous manner of claim 15 wherein said nucleic acid extraction cartridge is a multi-barrel nucleic acid extraction cartridge having a first barrel and a second barrel that contains a filter and/or a silica pack that may be located inside in one or more barrels.

* * * * *